(12) United States Patent
Neuman et al.

(10) Patent No.: US 9,776,014 B2
(45) Date of Patent: Oct. 3, 2017

(54) BONE ENHANCEMENT DEVICE AND METHOD

(71) Applicant: Magdent Ltd., Ramat-Gan (IL)

(72) Inventors: Moshe Neuman, Ramat-Gan (IL); Roni Daffan, Jerusalem (IL); Joseph Shechter, Holon (IL)

(73) Assignee: Magdent Ltd., Ramat-Gan (IL)

( * ) Notice: Subject to any disclaimer, the term of this patent is extended or adjusted under 35 U.S.C. 154(b) by 203 days.

(21) Appl. No.: 14/398,520

(22) PCT Filed: May 2, 2013

(86) PCT No.: PCT/IL2013/050370
§ 371 (c)(1),
(2) Date: Nov. 3, 2014

(87) PCT Pub. No.: WO2013/164824
PCT Pub. Date: Nov. 7, 2013

(65) Prior Publication Data
US 2015/0094521 A1    Apr. 2, 2015

Related U.S. Application Data

(60) Provisional application No. 61/641,995, filed on May 3, 2012.

(51) Int. Cl.
*A61N 2/04* (2006.01)
*A61C 8/00* (2006.01)
(Continued)

(52) U.S. Cl.
CPC .............. *A61N 2/02* (2013.01); *A61C 8/0006* (2013.01); *A61C 8/0007* (2013.01);
(Continued)

(58) Field of Classification Search
CPC .......... A61N 2/00; A61N 2/002; A61N 2/004; A61N 2/006; A61N 2/02; A61C 8/0006; A61C 8/0007
See application file for complete search history.

(56) References Cited

U.S. PATENT DOCUMENTS

| 3,893,462 A | 7/1975 | Manning |
| 4,315,503 A | 2/1982 | Ryaby et al. |
| (Continued) | | |

FOREIGN PATENT DOCUMENTS

| WO | WO 2009/019688 | 2/2009 |
| WO | WO 2011/051947 | 5/2011 |
| WO | WO 2013/164824 | 11/2013 |

OTHER PUBLICATIONS

Applicant-Initiated Interview Summary Dated Dec. 23, 2015 From the US Patent and Trademark Office Re. U.S. Appl. No. 13/503,854.
(Continued)

*Primary Examiner* — Charles A Marmor, II
*Assistant Examiner* — Thaddeus Cox

(57) ABSTRACT

There is provided in accordance with an exemplary embodiment of the invention a method of osteointegration of an implant into surrounding jaw-bone, the method comprising: applying a magnetic field around an implant, the magnetic field produced around the implant to a jaw-bone depth of up to at least about 7 mm, the magnetic field having a magnetic flux density of about 0.05-0.5 mT at up to at least about 2 mm from a surface of the implant, the magnetic field produced by a coil within the implant. A device adapted for insertion into a jawbone implant and for producing the magnetic field for bone enhancement of surrounding jaw-bone is also described.

26 Claims, 19 Drawing Sheets

(51) Int. Cl.
| | |
|---|---|
| A61N 2/02 | (2006.01) |
| A61C 8/02 | (2006.01) |
| A61C 13/00 | (2006.01) |
| A61N 2/00 | (2006.01) |
| A61C 1/00 | (2006.01) |

(52) U.S. Cl.
CPC ........ *A61C 13/001* (2013.01); *A61C 13/0012* (2013.01); *A61C 13/0015* (2013.01); *A61N 2/004* (2013.01); *A61C 1/0015* (2013.01); *A61C 2204/005* (2013.01)

(56) References Cited

U.S. PATENT DOCUMENTS

| | | | |
|---|---|---|---|
| 4,329,678 A * | 5/1982 | Hatfield | G08B 25/06 |
| | | | 307/107 |
| 5,292,252 A | 3/1994 | Nickerson et al. | |
| 6,032,677 A | 3/2000 | Blechman et al. | |
| 6,034,295 A | 3/2000 | Rehberg et al. | |
| 6,605,089 B1 | 8/2003 | Michelson | |
| 7,408,134 B1 * | 8/2008 | Shaw | G01D 1/18 |
| | | | 219/492 |
| 2002/0032472 A1 * | 3/2002 | Zarinetchi | A61N 1/3787 |
| | | | 607/61 |
| 2004/0176805 A1 | 9/2004 | Whelan et al. | |
| 2006/0265026 A1 | 11/2006 | Madjar et al. | |
| 2008/0129486 A1 * | 6/2008 | Jeckelmann | A61B 5/0002 |
| | | | 340/539.12 |
| 2010/0143871 A1 * | 6/2010 | Berger | A61B 17/8605 |
| | | | 433/174 |
| 2011/0151397 A1 * | 6/2011 | Seo | A61C 8/0048 |
| | | | 433/32 |
| 2012/0215281 A1 | 8/2012 | Neuman | |

OTHER PUBLICATIONS

Applicant-Initiated Interview Summary Dated Sep. 1, 2015 From the US Patent and Trademark Office Re. U.S. Appl. No. 13/503,854.
Communication Pursuant to Article 94(3) EPC Dated May 30, 2014 From the European Patent Office Re. Application No. 10826227.0.
International Preliminary Report on Patentability Dated Nov. 13, 2014 From the International Bureau of WIPO Re. Application No. PCT/IL2013/050370.
International Search Report and the Written Opinion Dated Aug. 12, 2013 From the International Searching Authority Re. Application No. PCT/IL2013/050370.
International Search Report and the Written Opinion Dated Mar. 15, 2011 From the International Searching Authority Re. Application No. PCT/IL2010/000897.
Notice of Non-Compliant Amendment (37 CFR 1.121) Dated Apr. 16, 2014 From the US Patent and Trademark Office Re. U.S. Appl. No. 13/503,854.
Official Action Dated Sep. 4, 2015 From the US Patent and Trademark Office Re. U.S. Appl. No. 13/503,854.
Official Action Dated May 6, 2014 From the US Patent and Trademark Office Re. U.S. Appl. No. 13/503,854.
Official Action Dated May 13, 2015 From the US Patent and Trademark Office Re. U.S. Appl. No. 13/503,854.
Official Action Dated Nov. 19, 2014 From the US Patent and Trademark Office Re. U.S. Appl. No. 13/503,854.
Restriction Official Action Dated Sep. 26, 2013 From the US Patent and Trademark Office Re. U.S. Appl. No. 13/503,854.
Supplementary European Search Report and the European Search Opinion Dated Oct. 14, 2013 From the European Patent Office Re. Application No. 10826227.0.
Barak et al. "A New Device for Improving Dental Implants Anchorage: A Histological and Micro-Computed Tomography Study in the Rabbit", Clinical Oral Implants Research, 00: 1-8, First Published Aug. 6, 2015.
Brighton et al. "Signal Transduction in Electrically Stimulated Bone Cells", The Journal of Bone and Joint Surgery, American vol., 83-A(10): 1514-1523, Oct. 2001.
Chang et al. "Effect of Pulse-Burst Electromagnetic Field Stimulation on Osteoblast Cell Activities", Bioelectromagnetics, 25(6): 457-465, Sep. 2004.
Esposito et al. "Interventions for Replacing Missing Teeth: Different Times for Loading Dental Implants", The Cochrane Database of Systemic Reviews, 1(Art.CD003878): 1-51, Jan. 21, 2009.
Fini et al. "The Effect of Pulsed Electromagnetic Fields on the Osteointegration of Hydroxyapatite Implants in Cancellous Bone: A Morphologic and Microstructural In Vivo Study", Journal of Orthopaedic Research, 20(4): 756-763, Jul. 2002.
Fu et al. "A Novel Single Pulsed Electromagnetic Field Stimulates Osteogenesis of Bone Marrow Mesenchymal Stem Cells and Bone Repair", PLoS One, 9(3): e91581-1-e91581-9, Mar. 14, 2014.
Gabet et al. "Endosseous Implant Anchorage Is Critically Dependent on Mechanostructural Determinants of Peri-Implant Bone Trabeculae", Journal of Bone and Mineral Research, 25(3): 575-583, Published Online Aug. 3, 2009.
Gabet et al. "Trabecular Bone Gradient in Rat Long Bone Metaphyses: Mathematical Modeling and Application to Morphometric Measurements and Correction of Implant Positioning", Journal of Bone and Mineral Research, 23(1): 48-57, Published Online Sep. 10, 2007.
Goldstein et al. "Electrical Stimulation for Facture Healing: Current Evidence", Journal of Orthopaedic Trauma, 24(3 Suppl.): S62-S65, Mar. 2010.
Gupta et al. "Pulsed Electromagnetic Stimulation of Nonunion of Tibial Diaphyseal Fractures", Indian Journal of Orthopaedics, 43(2): 156-160, Apr.-Jun. 2009.
Matsumoto et al. "Pulsed Electromagnetic Fields Promote Bone Formation Around Dental Implants Inserted Into Femur of Rabbits", Clinical Oral Implants Research, 11(4): 354-360, Aug. 2000.
Matsumoto et al. "Pulsed Electromagnetic Fields Promote Bone Formation Around Dental Implants Inserted Into the Femur of Rabbits", Clinical Oral Implants Research, 11: 354-360, 2000. Abstract, Table 1, p. 357, col. 1, Para 1, col. 2, Para 3—p. 358, col. 2, Para 5.
Matsumoto et al. "Pulsed Electromagnetic Fields Promote Bone Formation Around Dental Implants Inserted Into the Femur of Rabbits", Clinical Oral Implants Research, XP008155161, 11(4): 354-360, Jan. 1, 2000.
Munhoz et al. "Long-Term Rabbits Bone Response to Titanium Implants in the Presence of Inorganic Bovine-Derived Graft", Journal of Biomaterials Applications, 27(1): 91-98, Published Online Feb. 22, 2011.
Ongaro et al. "Pulsed Electromagnetic Fields Stimulate Osteogenic Differentiation in Human Bone Marrow and Adipose Tissue Derived Mesenchymal Stem Cells", Bioelectromagnetics, 35: 426-436, Published Online Aug. 6, 2014.
Ozen et al. "Evaluation of Pulsed Electromagnetic Fields on Bone Healing After Implant Placement in the Rabbit Mandibular Model", Turkish Journal of Medical Sciences, 34(2): 91-95, 2004.
Roland et al. "Effects of Pulsed Magnetic Energy on a Microsurgically Transferred Vessel", Plastic and Reconstructive Surgery, 105(4): 1371-1374, Apr. 2000.
Shupak et al. "Therapeutic Uses of Pulsed Magnetic-Field Exposure: A Review", The Radio Science Bulletin, 307: 9-32, Dec. 2003. p. 10.
Smith et al. "Microcirculatory Effects of Pulsde Electromagnetic Fields", Journal Orthopaedic Research, 22(1): 80-84, Jan. 2004.
Tawse-Smith et al. "Early Loading of Unsplinted Implants Supporting Mandibular Overdentures Using a One-Stage Operative Procedure With Two Different Implant Systems: A 2-Year Report", Clinical Implant Dentistry and Related Research, 4(1): 33-42, 2002.
Taylor et al. "Effect of Pulsed Electromagnetic Fields on Maturation of Regenerate Bone in a Rabbit Limb Lengthening Model", Journal of Orthopaedic Research, 24(1): 2-10, Published Online Oct. 27, 2005.
Wang et al. "Pulsed Electromagnetic Field May Accelerate In Vitro Endochondral Ossification", Bioelectromagnetics, 36(1): 35-44, Published Online Oct. 30, 2014.

(56) References Cited

OTHER PUBLICATIONS

Communication Pursuant to Article 94(3) EPC Dated May 2, 2016 From the European Patent Office Re. Application No. 10826227.0
Communication Pursuant to Article 94(3) EPC Dated Mar. 17, 2017 from the European Patent Office Re. Application No. 10826227.0 (6 pages).

* cited by examiner

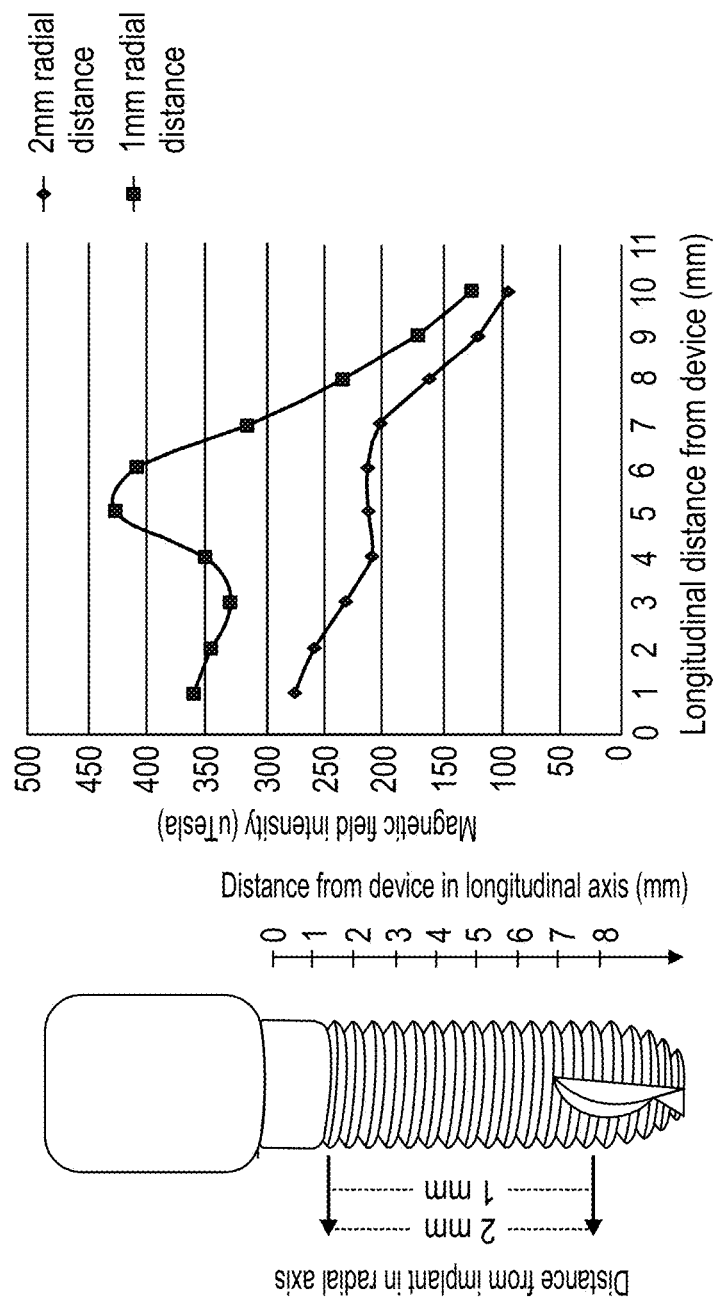

|  | 1 mm radial distance | | | 2 mm radial distance | | |
|---|---|---|---|---|---|---|
| Longitudinal distance | Z vector | R vector | Magnetic Intensity (uTesla) | Z vector | R vector | Magnetic Intensity (uTesla) |
| 1 mm | 227 | 290 | 350.5 | 225 | 161 | 276.7 |
| 2 mm | 331 | 102 | 346.4 | 250 | 68 | 259.1 |
| 3 mm | 314 | 97 | 328.6 | 229 | 42 | 232.8 |
| 4 mm | 225 | 272 | 353.0 | 161 | 136 | 210.8 |
| 5 mm | 119 | 408 | 425.0 | 65 | 204 | 214.1 |
| 6 mm | 42 | 408 | 410.2 | 32 | 212 | 214.4 |
| 7 mm | 110 | 297 | 316.7 | 81 | 187 | 203.8 |
| 8 mm | 136 | 194 | 235.9 | 86 | 140 | 164.3 |
| 9 mm | 127 | 121 | 175.4 | 81 | 99 | 123.3 |
| 10 mm | 105 | 74 | 129.3 | 70 | 68 | 97.6 |

FIG. 7C

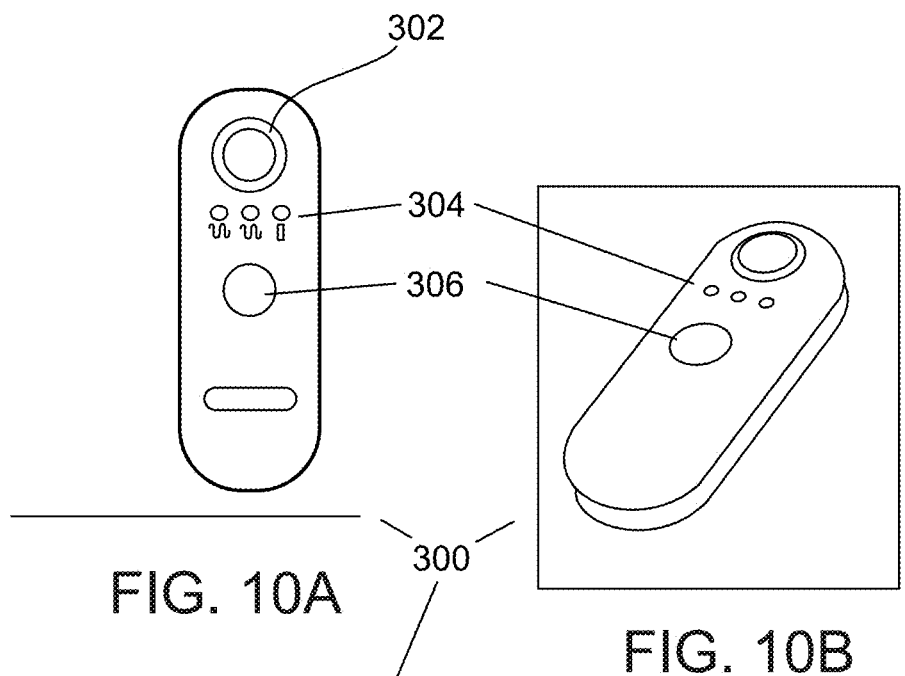
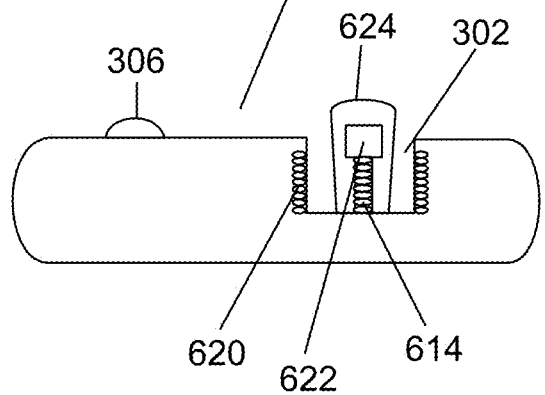
FIG. 10A
FIG. 10B
FIG. 10C

BONE ENHANCEMENT DEVICE AND METHOD

RELATED APPLICATIONS

This application is a National Phase of PCT Patent Application No. PCT/IL2013/050370 having International filing date of May 2, 2013, which claims the benefit of priority under 35 USC §119(e) of U.S. Provisional Patent Application No. 61/641,995 filed May 3, 2012.

This application is also related to PCT WO 2011/051947, entitled "IMPLANT DEVICE FOR STIMULATING OSTEOGENESIS AND OSSEOINTEGRATION", filed with the same common inventor Moshe NEUMAN. The contents of the above applications are all incorporated by reference as if fully set forth herein in their entirety.

FIELD AND BACKGROUND OF THE INVENTION

The present invention, in some embodiments thereof, relates to a medical implant device and, more particularly, but not exclusively, to a device for bone enhancement by application of electromagnetic fields.

U.S. Pat. No. 5,292,252 by Nickerson et al. disclose "A stimulator healing cap is disclosed for enhancing and speeding the growth of bone cells and bone tissue surrounding a dental implant."

Matsumoto, H et al. "Pulsed Electromagnetic Fields Promote Bone Formation around Dental Implants Inserted into the Femur of Rabbits", Clin Oral Impl Res 2000:11:354-360. discloses "These results suggest that PEMF stimulation may be useful for promoting bone formation around rough-surfaced dental implants."

Song J K et al. "An electronic device for accelerating bone formation in tissues surrounding a dental implant" Bioelectromagnetics. 2009 July; 30(5):374-84. disclose "Based on these results showing accelerated bone formation on and around the dental implant, it could be suggested that the latent time for osseointegration in dental implants can be reduced, and the success rate of implants in poor quality bone can be increased".

Additional background art includes:
U.S. patent application 2006/0265026 by Madjar et al.
U.S. Pat. No. 6,605,089 by Michelson et al.
U.S. patent application 2004/0176805 by Whelan et al.

SUMMARY OF THE INVENTION

An aspect of some embodiments of the invention relates to an enhancement device adapted to produce a magnetic field to enhance osseointegration of a jaw bone implant.

There is provided in accordance with an exemplary embodiment of the invention a method of osseointegration of an implant into surrounding jaw-bone, the method comprising:

applying a magnetic field around an implant, the magnetic field produced around the implant to a jaw-bone depth of up to at least about 7 mm, the magnetic field having a magnetic flux density of about 0.05-0.5 mT at up to at least about 2 mm from a surface of the implant, the magnetic field produced by a coil within the implant.

In an exemplary embodiment of the invention, the magnetic flux density is about 0.2-0.45 mT at up to at least about 1 mm from the surface.

In an exemplary embodiment of the invention, the magnetic flux density is about 0.2-0.3 mT at up to at least about 2 mm from the surface.

In an exemplary embodiment of the invention, applying comprises applying the magnetic field around at least 80% of the depth.

In an exemplary embodiment of the invention, applying comprises applying the magnetic field lines in a primarily parallel direction within +/−15 degrees to a long axis of the implant.

In an exemplary embodiment of the invention, applying comprises applying the magnetic field with a gradient perpendicular to the surface of the implant.

In an exemplary embodiment of the invention, the magnetic field varies over time with a frequency ranging from 0.5 Hz to 50 Hz.

In an exemplary embodiment of the invention, applying comprises applying a current pulse at a repetition rate of 0.5 Hz to 50 Hz.

In an exemplary embodiment of the invention, applying comprises producing a pulse duration of current that ranges from about 30 to 70 microseconds followed by a wait time that is 1500-2400 times as long as the pulse duration.

In an exemplary embodiment of the invention, applying comprises applying a sinusoidal pulse of current to produce the magnetic field.

In an exemplary embodiment of the invention, applying comprises applying a biphasic pulse of current to produce the magnetic field.

In an exemplary embodiment of the invention, applying comprises applying the magnetic field continuously for a period of 30 to 70 days.

In an exemplary embodiment of the invention, applying comprises applying a current to produce the magnetic field having a peak amplitude from 50 mA to 100 mA.

In an exemplary embodiment of the invention, the method further comprises deciding to enhance osseointegration of a dental implant into the jawbone.

In an exemplary embodiment of the invention, the depth of the implant comprises a portion of the implant only in contact with trabecular bone.

In an exemplary embodiment of the invention, applying a magnetic field around an implant is controlled by remote activation using an externally applied field.

There is provided in accordance with an exemplary embodiment of the invention a device adapted for insertion into a jawbone implant and for bone enhancement of surrounding jawbone, the device comprising:

a first transmitter arranged to transmit at least one of a magnetic and electric field for the bone enhancement; and a magnetic switch coupled to activate the first transmitter, the magnetic switch activated by an external magnetic field.

In an exemplary embodiment of the invention, the magnetic field is configured to promote osseointegration of the jaw bone implant in the jaw bone. Optionally, the jaw bone implant is a base for an artificial tooth.

In an exemplary embodiment of the invention, the first transmitter comprises a coil.

In an exemplary embodiment of the invention, at least a portion of the first transmitter is further arranged as a receiver, and the external magnetic field is received on the first transmitter. Optionally, the device further comprises an attenuator arranged to prevent self activation of the first transmitter.

In an exemplary embodiment of the invention, a system adapted for bone enhancement comprises:

an implantable device; and a second transmitter arranged to transmit the external magnetic field.

Optionally, the second transmitter is arranged as a coil having a central hole large enough for insertion of the implantable device therein. In an exemplary embodiment of the invention, the second transmitter is incorporated in a cradle shape and the implantable device is inserted into the central hole of the cradle. Optionally, the cradle is small enough to be placed inside the mouth.

In an exemplary embodiment of the invention, the cradle is arranged for testing the power level generated by the implantable device by measuring a current induced by the magnetic field on the transmitter coil.

In an exemplary embodiment of the invention, the cradle comprises an input for allowing remote activation of the implantable device by a user, and an output for allowing a user to determine a state of the implantable device.

In an exemplary embodiment of the invention, the external magnetic field is coded for programming a controller controlling the first transmitter, the controller disposed in the implantable device. Optionally or additionally, the external magnetic field is arranged for wirelessly charging batteries in the implantable device.

There is provided in accordance with an exemplary embodiment of the invention a device adapted for insertion into a jawbone implant and for bone enhancement of surrounding jawbone, the device comprising:

a wire coil wound and stacked around a core, the wire and the core arranged to produce a bone enhancing magnetic field in bone around the device, a number of turns of the wire, a diameter of the wire and a number of stacks arranged to reduce heating and increase the magnetic field.

In an exemplary embodiment of the invention, the wire and core are arranged to reduce heating of the surrounding bone.

In an exemplary embodiment of the invention, the device is sized and arranged for insertion in a jaw bone implant for an artificial tooth to reach to the end of a cavity in the implant.

In an exemplary embodiment of the invention, a diameter of the wire ranges from about 10 µm to about 80 µm.

In an exemplary embodiment of the invention, a diameter of the coil when wound around the core is about 800 µm to about 1150 µm.

In an exemplary embodiment of the invention, a number of turns of the wire around the core ranges from about 450 to about 550.

In an exemplary embodiment of the invention, the bone is heated by about 0.02 degrees Celsius to about 3 degrees Celsius during steady state.

In an exemplary embodiment of the invention, the heating of the bone and the magnetic field are selected to synergistically increase osteointegration in the bone.

In an exemplary embodiment of the invention, the device further comprises an outer screw sheath, the core contained within the outer screw sheath and the core removable from the sheath. Optionally, the screw sheath is adapted for direct engagement with bone. Optionally, the screw sheath is coated with one or more drugs.

There is provided in accordance with an exemplary embodiment of the invention an energy saving circuit configured for a bone enhancement device insertable in a jawbone implant, the circuit comprising:

a coil arranged to produce a bone enhancing magnetic field;

a capacitor in series with the coil, the capacitor being able to store sufficient charge to pass a current through the coil to produce the magnetic field;

one or more switches in series with the capacitor; and a controller to:

control the switches to maintain the capacitor at a first voltage value during a non-pulse phase, wherein no significant magnetic field is produced, control the switches to charge the capacitor to a second voltage value, the second voltage value equal to about the first voltage value, the second voltage value having a charge opposite to the first voltage value; and control the switches to charge the capacitor from the second voltage value back to the first voltage value, the charging occurring over a time period of a pulse phase, wherein the charging the capacitor comprises passing a current through the coil to produce the magnetic field, the current related to a voltage drop across the coil of about two times the first voltage.

In an exemplary embodiment of the invention, a ratio between the maintaining and the charging ranges from about 1:750 to about 1:5000.

In an exemplary embodiment of the invention, charging to the second voltage occurs within about 25 microseconds.

In an exemplary embodiment of the invention, charging back to the first voltage value occurs within about 25 microseconds.

In an exemplary embodiment of the invention, a voltage source of about 3 Volt is used.

In an exemplary embodiment of the invention, the current to produce the magnetic field reaches a peak to peak of about 130 mA.

In an exemplary embodiment of the invention, a peak current is reached during one voltage swing.

In an exemplary embodiment of the invention, a wait period between a first of the charging and a second of the charging is 750-5000 times the time taken for the first charging.

In an exemplary embodiment of the invention, energy not used in producing the magnetic field by the coil is collected in the capacitor and used for the next transmission.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings and/or images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 7A is a graph illustrating an exemplary magnetic field produced by the enhancement device, in accordance with an exemplary embodiment of the invention;

FIG. 7B is an image of an exemplary enhancement device to help understand the field as in FIG. 7A;

FIG. 7C is the raw data used of FIG. 7A in table format;

FIGS. 10A-10C are schematics of an activation cradle to control the enhancement device, in accordance with an exemplary embodiment of the invention;

DESCRIPTION OF SPECIFIC EMBODIMENTS OF THE INVENTION

Figure 1A:
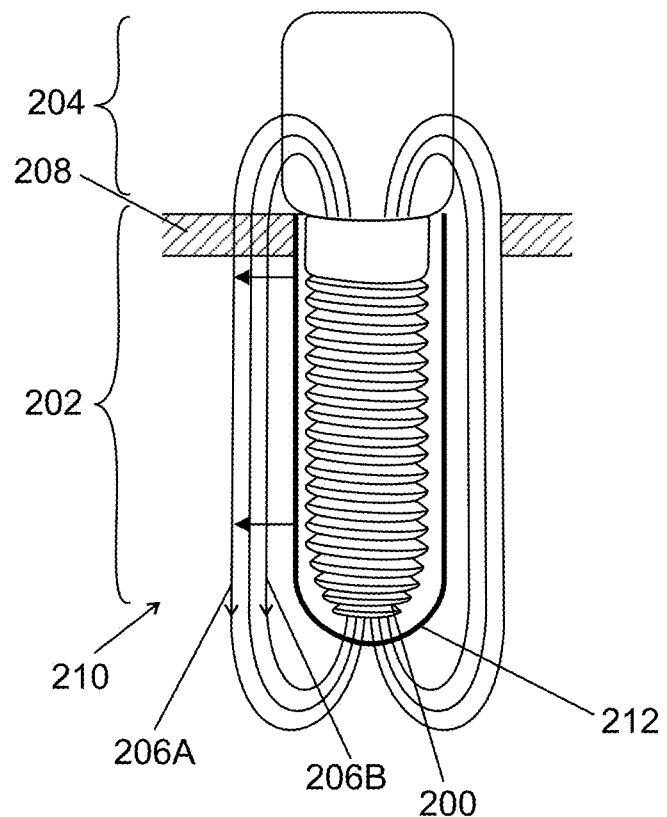
FIG. 1A is a schematic of an exemplary bone enhancement device, in accordance with an exemplary embodiment of the invention.

The present invention, in some embodiments thereof, relates to a medical implant device and, more particularly, but not exclusively, to a device for bone enhancement by application of electromagnetic fields.

An aspect of some embodiments of the invention relates to a method for enhancing and/or stimulating osteointegration of an implant to surrounding bone. In an exemplary embodiment of the invention, a dental implant is integrated into surrounding jaw bone (e.g., mandible, maxilla).

In an exemplary embodiment of the invention, the magnetic field is applied with a set of parameters, for example, the magnetic flux density is about 0.2-0.45 mT at up to about 1 mm from the surface implant, and/or the magnetic flux density is about 0.2-0.3 mT at up to about 2 mm from the surface.

In an exemplary embodiment of the invention, the magnetic field is at a gradient when measured perpendicular to the surface of the implant (e.g., within the first about 2 mm) For example, about 30 uTesla/mm, or about 50 uTesla/mm, or about 100 uTesla/mm, or about 150 uTesla/mm, or about 200 uTesla/mm, or about 250 uTesla/mm, or other smaller, intermediate or larger gradients.

In an exemplary embodiment of the invention, the magnetic field is at a gradient when measured parallel to the surface of the implant (e.g., within the first about 2 mm). For example, about 0 uTesla/mm, or 10 UTesla/mm, or about 25 uTesla/mm, or about 50 uTesla/mm, or about 75 uTesla/mm, or about 100 uTesla/mm, or about 150 uTesla/mm, or other intermediate or larger gradients. The gradient is either positive or negative, as in some places the magnetic field values increase and sometimes decrease.

In an exemplary embodiment of the invention, the magnetic flux density is located around at least, for example, about 90% of the length of the implant, or at least about 80% of the length, or at least about 70% of the length, or at least about 60% of the length, or at least about 50% of the length, or other smaller, intermediate or larger percentages. Alternatively or additionally, the magnetic field density is located at a jaw-bone depth (e.g., from the surface) of, for example, up to at least about 3 mm, or 4 mm, or 5 mm, or 7 mm, or 10 mm, or 13 mm, or other smaller, intermediate or larger depths.

In an exemplary embodiment of the invention, the method comprises applying an electromagnetic field to bone surrounding the implant. Optionally or additionally, the method comprises stimulating osteogenesis (e.g., new bone formation). Optionally or additionally, the method comprises enhancing bone turnover (e.g., the process of removing existing bone and replacing with new bone). Optionally or additionally, the method comprises stimulating and/or enhancing the activity of osteoclasts and/or osteoblasts. Optionally or additionally, the method comprises improving bone quality, for example, with patients with low bone density and/or weak bones (e.g., when compared to healthy patients). Optionally or additionally, the method comprises reducing the time required for integration of an implant into surrounding bones. Optionally or additionally, the method comprises improving osteointegration.

Some additional exemplary parameters are described in the section "Exemplary Magnetic Field Parameters". In an exemplary embodiment of the invention, the magnetic field is pulsed. The parameters causing the bone enhancement have been discovered by the inventors in an experiment.

In an exemplary embodiment of the invention, an electrical current is passed through a coil to produce the electromagnetic field. Optionally, the coil is positioned within the device so that the coil is surrounded by the bone outside of the implant, for example, the coil is not positioned within the cap of the device, the cap being located externally to the bone. Additionally or alternatively, at least a portion of the coil is positioned within a portion of the cap. For example, between 10-25% of the length of the coil such as 15%, 18% and or intermediate lengths is positioned within a portion of the cap. In some embodiments, the portion of the cap that comprises the coil is not surrounded by bone, for example positioned externally to the bone. In some embodiments, the dimensions of the coil within the cap portion may differ from the dimensions of the coil within the implant, for example the coil in the cap portion may have a larger diameter.

In some embodiments, the magnetic field through bone tissue is located outside of the coil. Optionally, the coil is located within the implant, and the magnetic field is located outside of the implant.

An aspect of some embodiments of the invention, relates to a jaw-bone enhancement device for insertion into a dental implant and/or directly into the jawbone, the device being adapted for producing a bone enhancing electromagnetic field. In an exemplary embodiment of the invention, the device comprises a wire wound around a core.

In an exemplary embodiment of the invention, the coiled wire is stacked around the core. Optionally, the number of wires in the stack, the number of windings around the core and/or the diameter of the wire are selected according to a tradeoff between increased wire heating (e.g., resistive heating with smaller diameter wires) and increased magnetic field (e.g., more windings produce a stronger magnetic field but require small diameter wires to be able to pack the windings inside the implant).

In an exemplary embodiment of the invention, some heat produced by the device is desired, for example, to improve local blood flow to the bone. For example, a temperature rise of at least 0.5 degrees Celsius in the nearby bone, or at least 1.0 degrees, or at least 2.0 degrees, or at least 3.0 degrees Celsius. The nearby bone is, for example, the bone affected by the electromagnetic field, for example, up to about 1 mm, or about 2 mm, or other smaller, intermediate or larger distances. The temperature rise may be especially desired in the jawbone, as the jawbone is cooled off, for example, by opening the mouth. In an exemplary embodiment of the invention, the heat and the magnetic field synergistically enhance osteointegration.

An aspect of some embodiments of the invention relates to a bone enhancement device, the device comprising a transmitter for producing a magnetic field to enhance surrounding bone. In an exemplary embodiment of the invention, the transmitter is activated or turned off or programmed by application of an external magnetic field to activate a magnetic switch.

In an exemplary embodiment of the invention, the transmitter for producing the magnetic fields and the receiver for receiving signals from the external magnetic fields share the same coil. Alternatively, the transmitter and receiver are different elements.

In an exemplary embodiment of the invention, the signal received by the coil is sensed by an input on the controller. If the signal is above a predefined threshold (e.g., voltage), a state change is trigger. If the signal is below the threshold, a state change is not triggered.

In an exemplary embodiment of the invention, an attenuator attenuates signals produced by the coil. Optionally, the attenuator allows some signals to pass to the controller and prevents some signals from reaching the controller, for example, to prevent unwanted controller activations during electromagnetic field production. In an exemplary embodiment of the invention, the attenuator is in electrical communication between the coil and the controller input. Optionally, the attenuator comprises one or more resistors. Optionally, the value of the attenuator is selected so that signals produced due to the coil induction from the external magnetic field are above the threshold (and so trigger the state change). Optionally or additionally, the value of the attenuator is selected so that signals produced from the controller output (e.g., driving the coil to produce the enhancement magnetic field) are below the threshold (e.g., to prevent self triggering).

In an exemplary embodiment of the invention, an external cradle comprises an external transmitter for activating the controller. Optionally, the external transmitter is arranged to have a central hole big enough to fit the enhancement device. Optionally, the cradle performs one or more functions, for example; testing the power level of the device, activating the device, programming the device, turning off the device. Optionally, the device is activated while still in the sterile package.

An aspect some embodiments of the invention relates to an energy saving circuit to provide a current to a coil to produce the enhancing electromagnetic field. In an exemplary embodiment of the invention, the circuit is designed to save energy in circuits having very short duty cycles, when the ratio between the time of the voltage swings and the time of maintaining the stable voltage is, for example, 1:750-1:5000, or 1:1500 to 1:2400, or 1:2000 to 1:2400, or other smaller, intermediate or larger values are used.

In an exemplary embodiment of the invention, device operates with the low duty but is still effective in bone enhancement.

In an exemplary embodiment of the invention, a capacitor in series with the coil is maintained at a charge stated during a non-pulse phase. The wait period is, for example, for about 0.001 seconds, 0.005 seconds, 0.01 seconds, 0.05 seconds, 0.1 seconds, about 0.5 seconds, about 1 second, about 1.5 seconds, about 2 seconds, or other smaller, intermediate or larger times. In an exemplary embodiment of the invention, the capacitor's voltage value is swung, from the initial voltage, to a value equal to the initial voltage but with an opposite charge, and then back to the initial charge state.

In an exemplary embodiment of the invention, the voltage swing drives a current through the coil to produce the current. Optionally, the current through the coil is driven by a voltage drop over the coil about double the initial voltage value.

In an exemplary embodiment of the invention, the peak current is obtained within one voltage swing. For example, as opposed to requiring a plurality of swings to reach the peak.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Enhancement Device

FIG. 1A is a schematic of a bone enhancement device 200, in accordance with an exemplary embodiment of the invention. In an exemplary embodiment of the invention, device 200 comprises of a bone implant portion 202 and an optional top portion 204. In an exemplary embodiment, portion 202 is adapted for insertion into a pre-existing jaw-bone implant 212, for example, an anchor for an artificial tooth. Alternatively, in some embodiments, portion 202 is adapted for direct insertion into bone, for example, by acting as a screw. In an exemplary embodiment, portion 202 comprises a coil to form a bone enhancing electromagnetic field.

In an exemplary embodiment, device 200 produces a magnetic field (shown as lines 206A-B). Optionally, the magnetic field is primarily in the phi direction, for example, parallel to the axial axis of portion 202 within about +/−5 degrees, or +/−15 degrees, or +/−30 degrees, or other smaller, intermediate or larger variations from parallel. The direction of the magnetic field is related to the direction of the current through a coil located in portion 202 (detailed of coil are described herein), and in some embodiments, is reversed.

In an exemplary embodiment of the invention, the electromagnetic field enhances the bone remodeling and/or bone formation process. It is hypothesized that the electromagnetic field increases the activity of osteoblasts and/or osteoclasts, for example, to remove old and/or damaged bone and/or deposit new bone (e.g., bone turnover). In an exemplary embodiment of the invention, the electromagnetic field helps in osteointegration, in the attachment of bone implant 212 to the surrounding bone (e.g., trabecular bone 210). Optionally or alternatively or additionally, the electromagnetic field helps in osteointegration of bone implant 212 to surrounding cortical bone 208. It is hypothesized that the electromagnetic field reduces the time for integration of implant 212, for example, from about 3-6 months to about 1-2 months. It is further hypothesized that the electromagnetic field allows attachment of implant 212 to surrounding bone 210 in patients with poor bone quality, for example, by increasing the quality of the bone (e.g., bone density).

In an exemplary embodiment, top portion 204 houses batteries, circuitry and/or other control components. Optionally, portion 204 remains outside the bone (e.g., at least in part). Additional details of portion 204 are provided, for example, with reference to FIGS. 4A-4C.

In some embodiments, the enhancement device is coated with one or more drugs. Optionally, bottom portion 202 and/or an external sheath designed for direct insertion into bone is coated. Not necessarily limiting examples of drugs include; osteointegration enhancement drugs, antibiotics, cellular nutrients, anti-osteoporosis medications, vasodilators.

Figure 2:
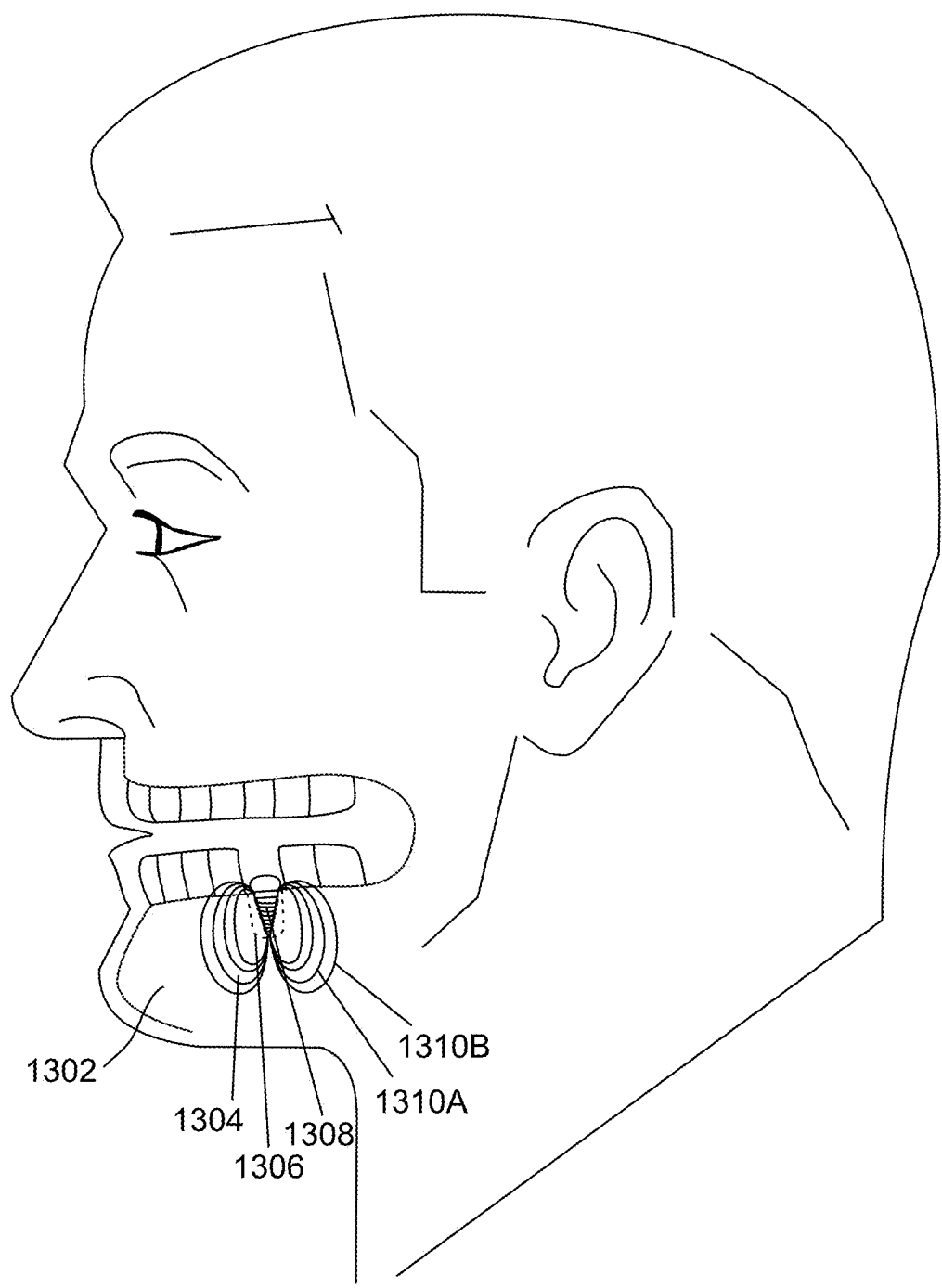
FIG. 2 is a schematic showing implantation of the enhancement device inside a jawbone implant, in accordance with an exemplary embodiment of the invention.

FIG. 2 is an illustration of a bone enhancement device 1308 to enhance integration of implant 1306 in jaw bone 1302 (e.g., mandible or maxilla), in accordance with an exemplary embodiment of the invention. In an exemplary embodiment, device 1308 produces magnetic fields (e.g., shown as lines 1310A-B). Optionally, the field acts on surrounding bone 1304. Optionally, the enhanced bone improves integration of implant 1306 into mandible 1302. Optionally, device 1308 is removed and replaced with an artificial tooth.

In some embodiments, two or more devices 1308 are implanted side by side, for example, to replace two teeth. Optionally, the implants are sufficiently far apart so that the therapeutic region of the magnetic fields do not overlap. Alternatively, the implants are close enough so that the magnetic fields overlap. Potentially the overlap in the magnetic field provides additional bone enhancement to the thin bone region.

Figure 1B:
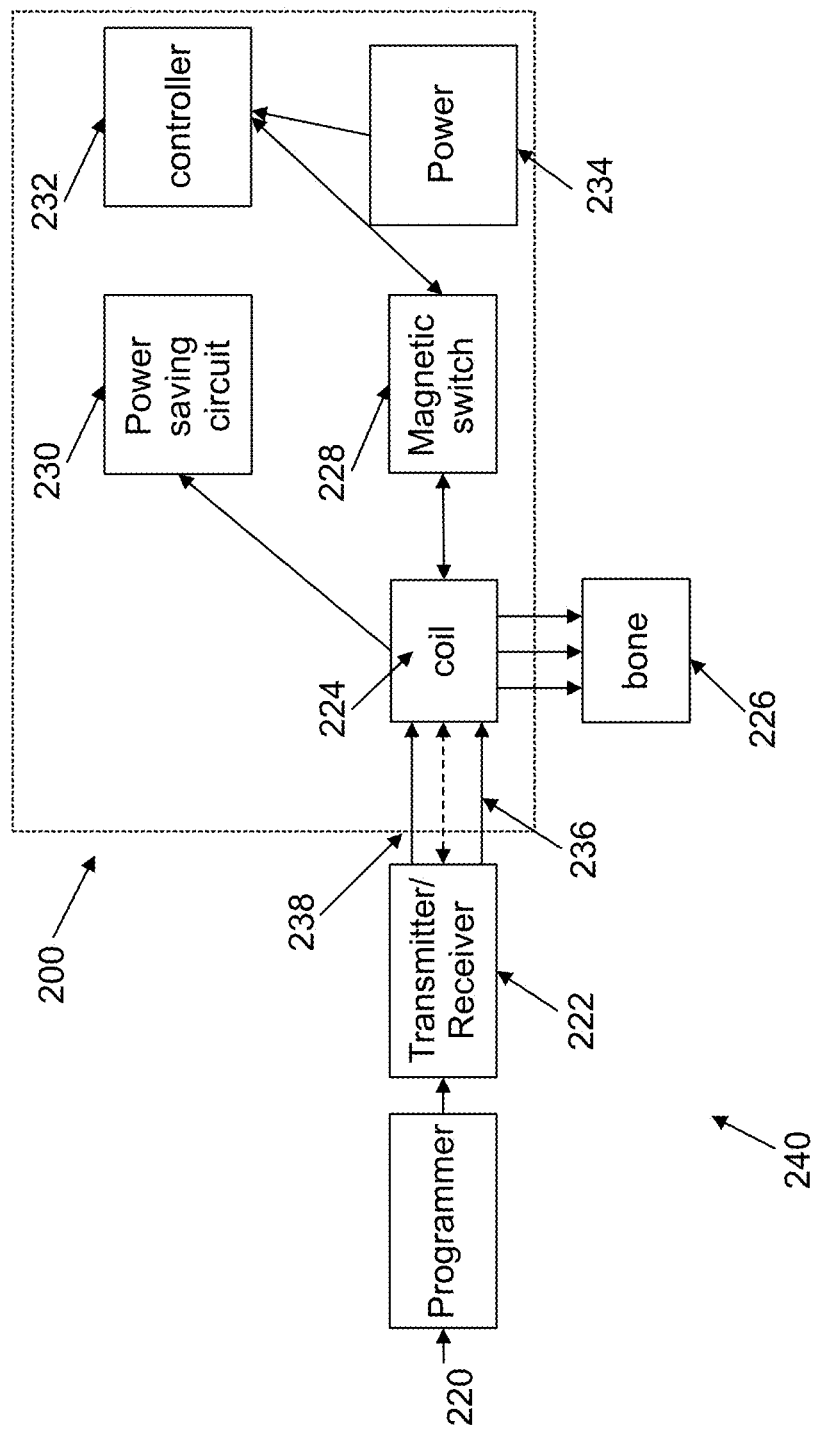
FIG. 1B is a block diagram of a bone enhancement system, in accordance with an exemplary embodiment of the invention.
Figure 14:
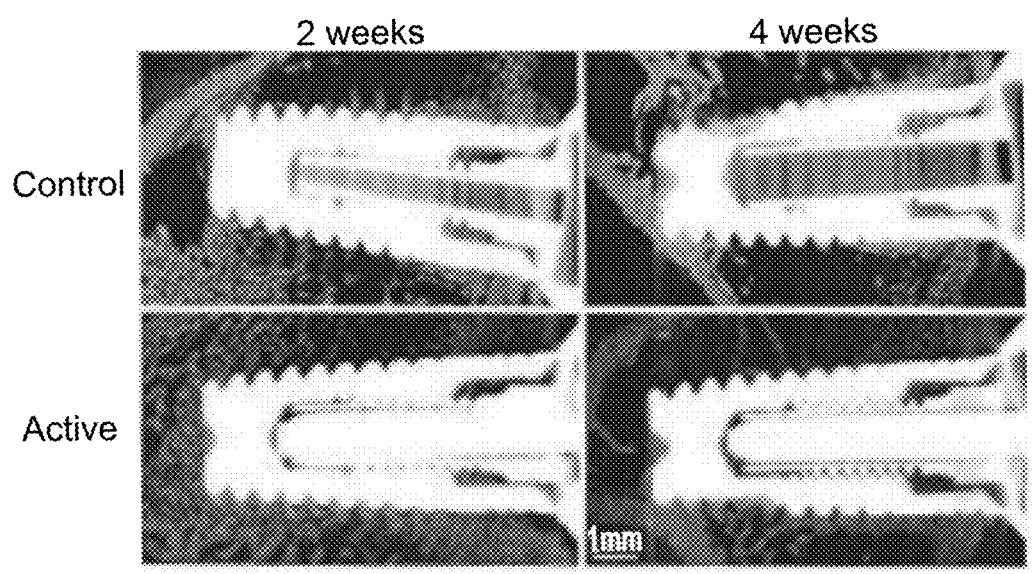
FIG. 14 shows some exemplary CT scans to help understand the experimental results.

FIG. 1B is a block diagram of a bone enhancement system 240, in accordance with an exemplary embodiment of the invention. System 240 is briefly described in broad terms, the details of which will be described herein. In exemplary embodiment of the invention, the device is screwed in to the bone implant, for example, after the implant has been inserted into the bone. FIG. 14 (described below) shows some CT images of the exemplary device inserted in the bone implant.

In an exemplary embodiment of the invention, different enhancement devices are available to fit different standard implant designs. For example, devices are designed in different sizes and/or shapes to fit the different implants. Alternatively, an adaptor is available to allow the enhancement device to be compatible with the different designs.

In an exemplary embodiment of the invention, device 200 comprises a coil 224 to generate an electromagnetic field 236 to enhance surrounding bone 226.

In some embodiments of the invention, an optional controller 232 controls application of current through coil 224. An optional power saving circuit 230 utilizes a power source 234 (e.g., batteries) in an energy efficient manner to control the current through coil 224 to generate field 236. Potentially, circuit 230 reduces the energy consumption, allowing device 200 to operate for longer periods of time. Optionally, controller is programmable, for example, by the physician. Alternatively or additionally, the physician selects a preset controller from a set of controllers according to the selected treatment.

In an exemplary embodiment of the invention, device 200 is activated when needed, for example, before insertion into the patient. Optionally, device 200 is activated by triggering a magnetic switch 228. Optionally, switch 228 turns controller 232 on (e.g., changes from sleep state to active state). Optionally or additionally, switch 228 turns off device 200, for example, by turning off controller 232.

In an exemplary embodiment of the invention, switch 228 is externally triggered. In an exemplary embodiment of the invention, an externally applied magnetic field 238 triggers switch 238. Optionally, field 238 is formed by a transmitter/receiver 222, optionally controlled by a programmer 220. In some embodiments, transmitter/receiver 222 detects electromagnetic field 236 produced by an active coil 224.

Potentially, external triggering allows activation of device 200 when needed, allowing further saving of power. Potentially, the shelf life of device 200 is increased by controlled activation. In an exemplary embodiment of the invention, a single pulse can be applied to the jaw without triggering activation of the device. Optionally, the attenuator is used to select the pulse to activate the programmer, the externally activated pulse having enough energy to pass the attenuator, with the pulse to produce the magnetic field not having sufficient energy to pass the attenuator.

Exemplary Method

Figure 3:
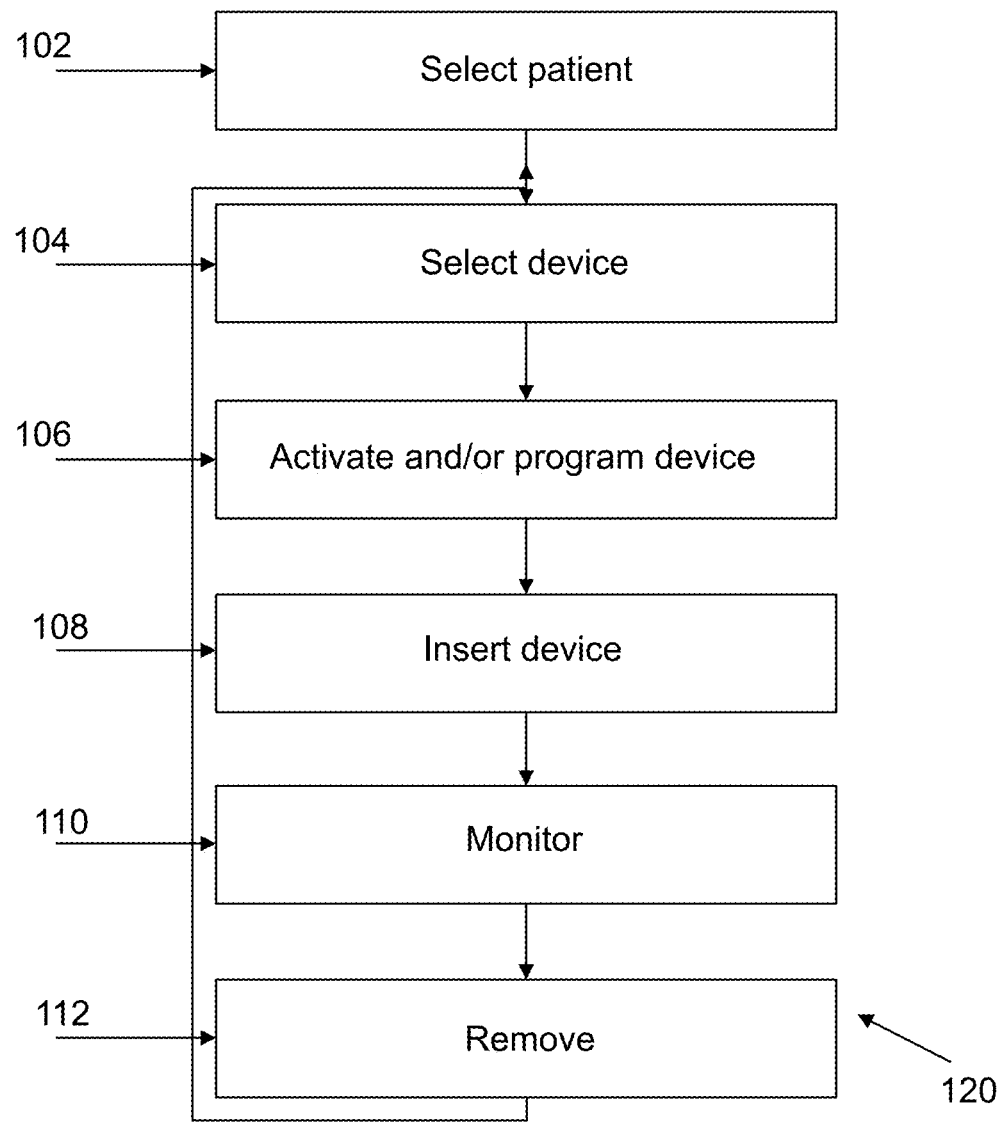
FIG. 3 is a method of treatment using the enhancement device, in accordance with an exemplary embodiment of the invention.

FIG. 3 is a flowchart of an exemplary method of treatment of a patient using the enhancement device, in accordance with an exemplary embodiment of the invention.

Optionally, at box 102, a patient (e.g., human or other animal mammal) is selected for treatment by the treatment device. The patient is selected, for example, by the physician or dentist. In some embodiments, the patient is selected for an artificial tooth implant.

In an exemplary embodiment of the invention, the patient is selected according to one or more bone problem indications, not necessarily limiting examples include; poor bone quality, insufficient bone density (e.g., osteoporosis), old age. Potentially, the enhancement device improves bone integration and/or healing in patients with the weak bones.

Alternatively, patients that do not suffer from bone problems may be selected for treatment. Potentially, the enhancement device reduces integration and/or healing time.

In some embodiments, the tooth can be placed over the cap of the enhancement device while the device is working to improve bone enhancement. Optionally, the tooth cap is removed after the treatment period (e.g., 2 months), the enhancement device is removed, and the tooth cap is replaced.

In an exemplary embodiment of the invention, the patient is selected according to the bone site requiring enhanced healing and/or strengthening. Optionally, the bone site requires enhancement to attach to an inserted prosthesis. For example, a dental implant (e.g., to support an artificial tooth) inserted into the jaw bone.

Optionally, at box 104, the device for insertion into the patient is selected. In an exemplary embodiment of the invention, the device is selected to produce a selected enhancement magnetic field in the bone. Further details of the device are, for example, provided in the section "Exemplary Device".

Optionally, at box 106, the device is activated before insertion into the patient. In an exemplary embodiment of the invention, the device is activated (e.g., switched from a sleep state to an active state) by the dentist immediately before insertion by a wireless activator, for example, as described in the section "Magnetic Switch". Alternatively, the device is activated by the manufacturer.

In some embodiments, the device is programmed as part of the activation and/or after the activation, for example, by the wireless activator. For example, the strength of the magnetic field and/or the current frequency and/or the on/off times are programmed, for example, by using the cradle as described in the section "EXEMPLARY MAGNETIC SWITCH".

At box 108, the device is inserted into the patient. In an exemplary embodiment of the invention, the device is inserted into a hole or hollow within an already implanted device, for example, a dental implant in the jawbone. Alternatively, the device is inserted directly into the jawbone, for example, by screwing or hammering the device into the bone.

Optionally, at 110, the enhancement effect of the device is monitored. Optionally, imaging is used to estimate the healing of bone and/or new bone formation, for example, CT or X-rays, for example, as described in the section "Experiment". In some embodiments, the images are compared to one another to determine the improvement, for example, relative to a pretreatment baseline.

In some embodiments, the monitoring occurs throughout the treatment period, for example, after about 2 weeks, or about 4 weeks, or about 6 weeks, or about 12 weeks, or other smaller, intermediate or larger time periods. Alternatively or additionally, the monitoring occurs at the end of the treatment period.

Optionally, at 112, the enhancement device is removed after the enhancement period (e.g., once the bone has sufficiently healed and/or reformed). For example, the device is removed from the jaw implant to allow insertion of the tooth prosthesis. Alternatively, the enhancement device is left in place, for example, if removal would require surgery (e.g., inside bone fixation devices).

Optionally, at 120, one or more steps are repeated, for example, if the batteries ran out in the device but the patient requires a longer treatment period, the current device is removed and replaced. In another example, if treatment is not proceeding as expected during monitoring at 110, another device with different magnetic field parameters is inserted to try to improve the healing, or the same device is adjusted and/or reprogrammed with different magnetic field parameters.

Exemplary Device

Figure 4A:
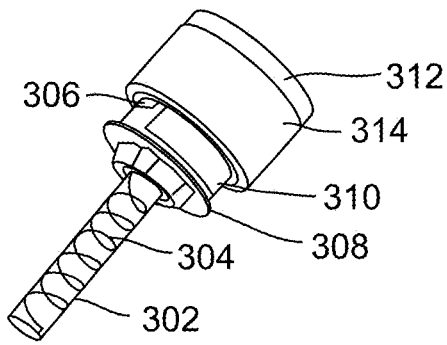
FIGS. 4A-4D are isometric views of various assembly levels of the enhancement device, in accordance with an exemplary embodiment of the invention.
Figure 4B:
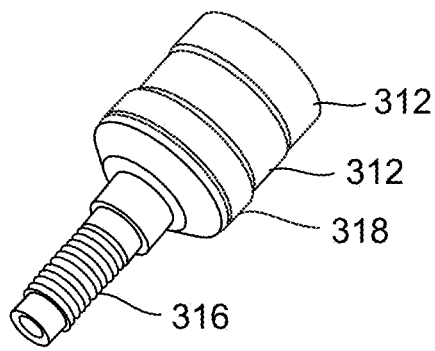
Figure 4C:
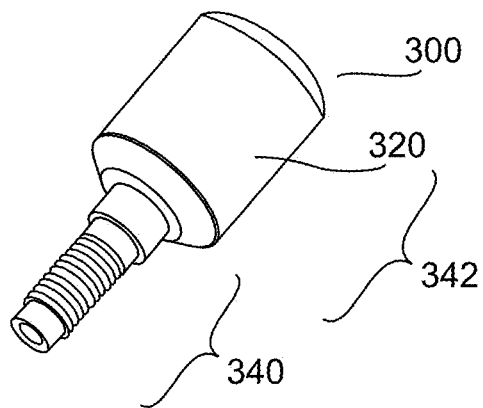
Figure 4D:
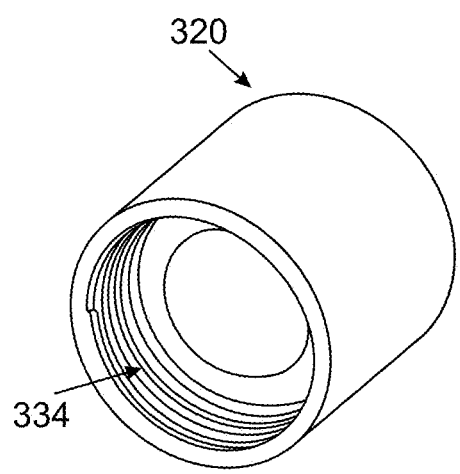
Figure 5A:
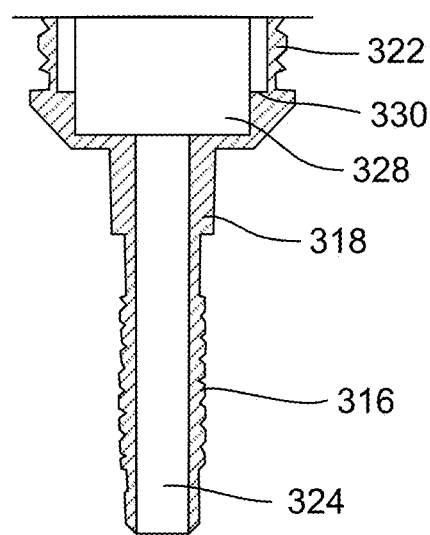
FIGS. 5A-5C are cross sectional views of the enhancement device, in accordance with an exemplary embodiment of the invention.
Figure 5B:
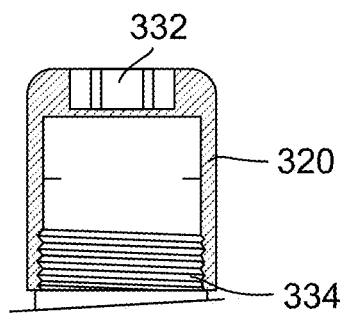
Figure 5C:
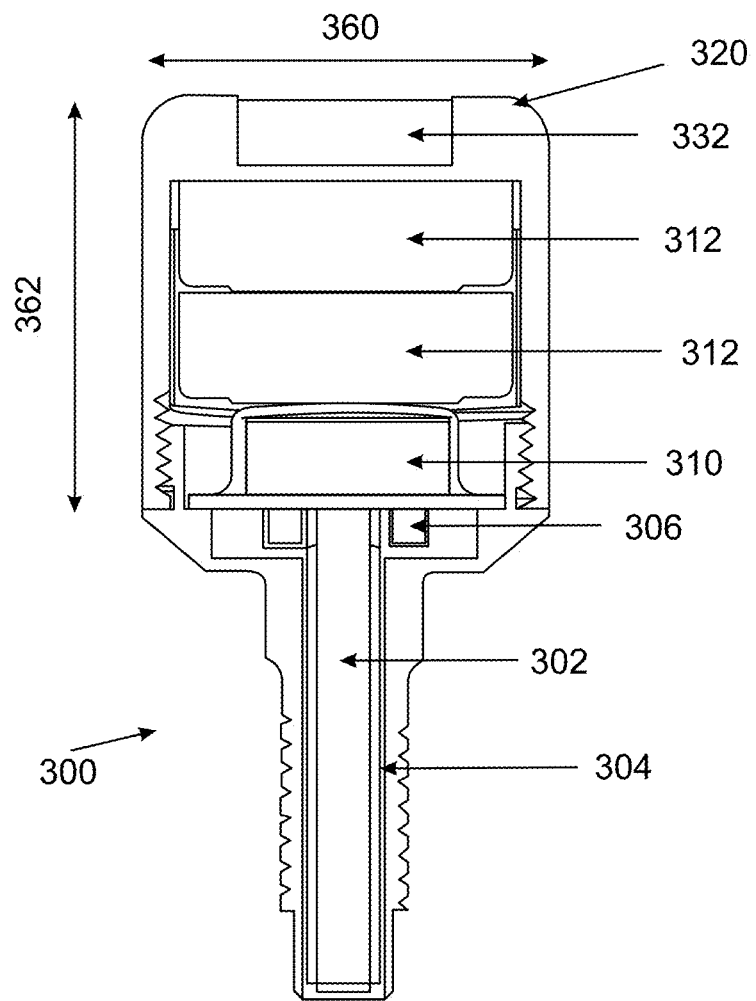

FIGS. 4A-4C are isometric views of an exemplary enhancement device 300 at various stages of assembly, in accordance with an exemplary embodiment of the invention. FIG. 4D is an enlarged view of the top cap, according to some embodiments of the invention. FIGS. 5A-5C are cross sectional views of parts of the enhancement device, in accordance with an exemplary embodiment of the invention. In an exemplary embodiment of the invention, the enhancement device is designed to be inserted into a dental implant located in the jaw bone (e.g., to secure an artificial tooth). Optionally, the device is inserted into the dental implant. In an exemplary embodiment of the invention, the enhancement device produces a magnetic field to enhance bone growth around the implant to improve adherence of the implant to the bone. Optionally or additionally, vibrations are produced, for example, by the core reacting to the field and/or heat.

Referring to FIG. 4A, a coil 304 is wound around a rod shaped extension 302. Further details of coil 304 are described, for example, with reference to FIG. 6. Optionally, a printed circuit board 308 is disposed at a proximal end of extension 302. Optionally, on one side of board 308 (e.g., closer to extension 302) are electrical components 306, for example, resistors, capacitors and/or transducers. Optionally, on the opposite side of board 308 is disposed a controller 310. Circuit diagrams detailing the interactions between controller 310, components 306 and coil 304 are described, for example, with reference to FIGS. 9 and/or 11. In an exemplary embodiment of the invention, one or more batteries 312 are disposed next to controller 310. Optionally, batteries are encased in a cylindrical contact 314. In an exemplary embodiment of the invention, the batteries are selected to last until the device can be replaced with the permanent implant, for example, at least 30 days, at least 50 days, at least 70 days, at least 100 days, or other smaller, intermediate or larger time frames. In a not necessarily limiting example, there are two batteries, each producing about 1.55 Volt (for a total of about 3 Volt), or the total voltage ranges from about 1.2 Volt-3.2 Volt, and/or the batteries have a rated capacity of about 8.3 mAh, or about 5 mAh-10 mAh, or other smaller, intermediate or larger voltages and/or capacities are used.

In some embodiments, rod shaped extension 302 comprises a separate unit, for example not connected directly to other components such as controller 310 and/or electrical components 306 and/or batteries 312. Optionally, coil 304 within rod 302 acts both as a transmitter of the magnetic field and as a receiver of the activation signals. In an exemplary embodiment, an externally applied magnetic and/or electromagnetic field is applied from a distance, for example activating a switch which enables the passing of a current pulse through coil 304. Optionally, the magnetic field activates controller 310, which controls the current passing through coil 304. Optionally, in such a case, rod 302 comprising coil 304 is implanted in a bone on its own, while other components of the device such as controller 310 and/or batteries 312 are positioned externally to the bone, for example outside the mouth. Alternatively, in some embodiments, rod shaped extension 302 and batteries 312 are connected directly, and controller 310 remotely activates the coil within rod shaped extension 302 and/or the batteries from a distance, for example turning the device on or off. In some embodiments, controller 310 charges batteries 312 by wireless connection.

FIG. 4B illustrates the partly assembled device of FIG. 4A, fitted with a bottom cap 318. Extension 304 with wound coil 302 is placed inside bore of cap 318. In an exemplary embodiment of the invention cap 318 comprises an outer screw 316. Optionally, screw 316 is adapted for threading inside an implant, for example, the dental implant. Alternatively or additionally, in some embodiments, coil 304 is wrapped around screw 316.

FIG. 4C illustrates the final assembled enhancement device 300. The partly assembled device of FIG. 4B is fitted with a top cap 320 (e.g., fits over batteries 312). An enlarged view of top cap 320 is shown in FIG. 4D. Optionally, top cap 320 is joined to bottom cap 318 by bottom cap threads 322 (shown in FIG. 5A) and matching top cap threads 334 (shown in FIG. 4D and in FIG. 5B). In some embodiments, the threading which connects the top and bottom caps is opposite to the threading of screw 316 into the bone. For example, the threading direction of the top and bottom caps is counterclockwise, and the threading direction of screw 316 is clockwise. A potential advantage of the opposite threading includes preventing disengagement of the top and bottom caps outside the dental implant during threading of screw 316.

In an exemplary embodiment of the invention, device 300 comprises a shaft 340 and a cap 342. As described, shaft 340 is inserted into the bone implant, and is surrounded by bone when deployed. Optionally, cap 342 is located outside of the implant and outside of the bone. Optionally, cap 342 has a size similar to a tooth to fit between adjacent teeth in the patient's mouth. In a not necessarily limiting example, shaft 340 is designed to fit into a standard bone implant having an external diameter of, for example, about 3.4-3.7 mm, an internal diameter of, for example, about 1.2 mm, an external height of, for example, about 10-11 mm and an internal height of, for example, about 7.8 mm.

FIG. 5A is a cross section of bottom cap 318. In an exemplary embodiment of the invention, cap 318 comprises screw 316 having a bore 324 therein sized to fit extension 304 and coil 302. Optionally, cap 318 comprises chamber 328 to house one or more control components. Optionally, printed circuit board 308 is secured in position on a flange 330.

FIG. 5B is a cross section of top cap 320. In an exemplary embodiment of the invention, cap 320 contains a release port 332 to allow insertion and/or removal of device 300 from the bone implant. Optionally, port 332 is hexagonal shape to allow rotation of screw 316 by a suitably shaped tool (e.g., commonly available). Optionally, port 332 comprises an internal thread.

Additionally and/or alternatively, in some embodiments, a face of cap 320 such as the top face is shaped to engage a tool, for example having a hexagonal shape which may be engaged by a suitably shaped tool, for example a socket wrench. Optionally, the shaped top face limits the need for an additional element for engaging a tool, therefore a shorter cap may be used. In some embodiments, the top face of cap 320 comprises an external thread.

In an exemplary embodiment of the invention, bottom cap 318 and/or top cap 320 are made from a biocompatible material, for example, titanium alloy. In an exemplary embodiment of the invention, the material is selected to have a relatively low conductivity (e.g., as compared to other metals) to reduce the formation of eddy currents therein.

FIG. 5C is a cross section of enhancement device 300, according to some embodiments of the invention. In some embodiments, as previously described, the device includes batteries 312, controller 310, a coil 304 wound around rod shaped extension 302, and electrical components 306. In some embodiments, as previously described, top cap 320 comprises a port 332.

In some embodiments, coil 304 extends along rod shaped extension 302. In some embodiments, coil 304 extends within a portion of the cap.

In a not necessarily limiting example, the size of cap 320 designed to fit in a jaw implant and between teeth has an external diameter 360 of, for example, about 5.8 mm and a height 362 of, for example, about 5-6 mm. In some embodiments, the size of external diameter 360 ranges between 3-7 mm, for example 3.5, 4.2, 6.1 mm or intermediate sizes. In some embodiments, the size of height 362 ranges between 3-8 mm, for example 3.2, 5.5, 7.8 mm.

Exemplary Device Parameters

Referring back to FIGS. 4A-4D, in an exemplary embodiment of the invention, current through coil 302 produces an electromagnetic field in the surrounding bone. Inventors discovered device designs that produce an electromagnetic field that enhances bone, for example, reduces the amount of time that a dental implant requires to be secured in the jaw bone.

Figure 6:
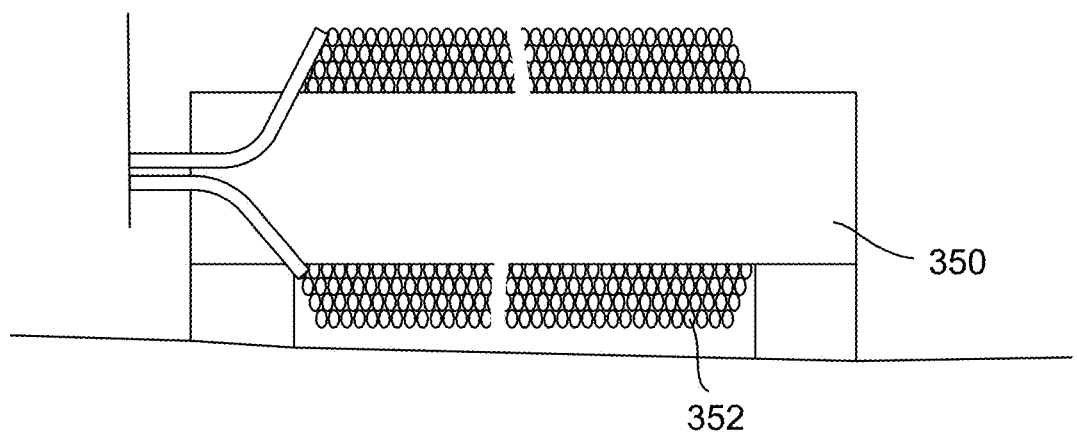
FIG. 6 is a cross sectional view of the ferrite core and winding wire of the enhancement device, in accordance with an exemplary embodiment of the invention.

FIG. 6 illustrates the discovered design of wound coil 304. In an exemplary embodiment of the invention, wound coil 304 comprises a wire 352 wound around a core 350. In an exemplary embodiment of the invention, wire 352 is wound around the circumference of core 350.

In an exemplary embodiment of the invention, the wire is made from electrically conductive materials, for example, copper, silver, aluminum, gold.

In an exemplary embodiment of the invention, the wire parameters are:
  Wire diameter of, for example, about 10-80 micrometers, or about 10-20 micrometers, or about 40-80 micrometers, or about 10-40 micrometers, or other smaller, intermediate or larger diameters.
  Stacked layers of the wire when wound around the core, for example, 1-10 layers, or about 2-6 layers, or about 4-5 layers, or other smaller, intermediate or larger number of layers.
  Each of the stacked layers has, for example, about 100-150 turns around the core, or about 125-133 turns, or other smaller, intermediate or larger numbers of turns. In an exemplary embodiment, the turns are arranged along the long axis of the core. In an exemplary embodiment of the invention the total number of wire turns is, for example, about 300-600, or about 450-550, or other smaller, intermediate or larger number of turns.

The diameter of the coil (e.g., when wound around the core) is, for example, about 0.5-1.5 mm, or about 0.8 mm to about 1.15 mm, or other smaller, intermediate or larger diameters.

Inventors discovered that the stacked coiling design produced a magnetic field that enhances the osteointegration of the implant in bone, for example, as described below in the section "EXPERIMENT".

In an exemplary embodiment of the invention, the device is programmed to produce a desired amount of heat. Alternatively or additionally, the device is built to have a certain heat output. Optionally, the heat generated by resistive heating of the coil is controlled and/or selected. Optionally, the temperature in the bone around the tissue is raised to a preselected value at a steady state of operation, for example, to no more than about 0.02 degrees Celsius, or no more than about 0.1 degrees, or no more than about 0.2 degrees, or no more than about 0.3 degrees, or no more than about 0.5 degrees Celsius, or no more than about 1.0 degrees, or no more than about 1.5 degrees, or no more than about 2 degrees, or no more than about 3 degrees, or other smaller, intermediate or larger temperature rises. Optionally, the temperature is raised in the bone within about 1 mm of the implant surface, or about 2 mm, or about 3 mm, or other smaller, intermediate or larger dimensions.

To help with understanding of the resistive heating, a short explanation of the underlying theory is provided. Even if the theory is incorrect, it does not preclude the working of embodiments of the invention as described. Note that the explanation relates to the exemplary embodiment, and may not be accurate for other embodiments.

The coil resistance R is related to the wire radius a, winding radius r and number of turns N by:

$$R = ro * N * 2\pi r / (pi * a^2)$$

Where ro is the resistivity of the coil wire material.
The dissipated heat $W_J$ is given by $$W_J = R \int I(t)^2 dt$$

Where R is the resistance, I is the current, and the integration is over the pulse duration.

The equations show that the magnetic field intensity is independent of the wire diameter, as long as the packing volume and energy consumption are the same. However, the wire diameter and number of turns affect the resistive loss and heating. Inventors estimate that if using a coil with 532 turns and wire diameter of 40 µm, and applying a current at a frequency of 10 Hz, the heating rate is less than about 0.02° C. in steady state operation. In this case, the overall coil impedance is much more affected by the ferromagnetic core response to the eddy currents.

In an exemplary embodiment of the invention, the coil design accounts for the desired overall inductance of the coil and/or ferromagnetic core complex. Potentially, a wide range of wire diameters and/or number of turns may be used.

Inventors estimate that using the wire diameter of 10 µm and repetition rate of 10 Hz, the heating rate may reach 0.3° C. in steady state operation.

In an exemplary embodiment of the invention, heating is reduced. Alternatively, heating is elevated. For example, the design is selected not to go over a temperature of, for example, about 2 degrees Celsius during steady state operation, or about 1.5 degrees Celsius, or about 1 degrees Celsius, or about 0.5 degrees Celsius, or other smaller, intermediate or larger temperatures.

In an exemplary embodiment of the invention, the heat from operation of the device and the produced magnetic fields cause a synergistic effect on bone enhancement. Optionally, a small amount of heat is selectively introduced into the surrounding tissue. Inventors hypothesize that the heating helps improve the bone enhancing effects, for example, by increasing blood flow to the bone region next to the implant.

Some embodiments of the enhancement device are especially good for the jaw, because the produced heat helps offset cooling of the device and/or surrounding bone, for example, conductive cooling caused by opening of the mouth and introduction of cooled air around the implant. Without being bound to theory, the magnetic fields improve bone turnover and/or formation, with the heat helping to increase blood flow and bring the needed raw materials and/or remove waste from the bone enhancement site are faster rates. However, some embodiments of the device can also be used in other items, for example, orthopedic devices such as nails and/or plates (e.g., for fracture fixation). Optionally, the orthopedic devices comprise a hollow inside, and the head of the enhancement device is the same diameter as the hollow, for example, so that the enhancement device is insertable therein. Optionally, the enhancement device is easily removable from the body, for example, there are wires extending from the enhancement device to outside of the body.

Inventors discovered that wrapping the coil around a ferromagnetic core provides for the bone enhancing magnetic field. For example, when using settings according to the exemplary embodiment, use of the core increases the magnetic flux density at a distance of about 2 mm from the outer device edge by about 5-10 fold, or by about 6-7 fold, or other smaller, intermediate or larger values.

In an exemplary embodiment of the invention, core 350 is made from a ferromagnetic material. Not necessarily limiting examples include; ferrite, iron, iron powder, laminated silicon steel, amorphous metals or any other type of suitable ferromagnetic material.

In an exemplary embodiment of the invention, the length of the ferrite is sized to fit into the interior of the screw portion of the bottom cap, for example, about 5-10 mm, or about 6-8 mm, or about 5.5-7.5 mm or other smaller, intermediate or larger sizes. Optionally, the core is sized according to available space in the implant, which in some embodiments reaches the tip of the implant and in some embodiments does not.

In an exemplary embodiment of the invention, the diameter of the ferrite is sized to fit into the interior of the screw portion of the bottom cap, for example, about 0.5-1.0 mm or about 0.6-0.75 mm, or other smaller, intermediate or larger sizes.

In an exemplary embodiment of the invention, the effective magnetic permeability (e.g., relative permeability, or $\mu_r$) is, for example, at least 40, or at least 100, or at least 500, or at least 1000, or other smaller, intermediate or larger values. Inventors hypothesize that a relatively higher magnetic permeability will produce a relatively higher magnetic flux density.

Inventors discovered that the cap surrounding core 350 (e.g., cap 318 made from titanium) increases eddy current formation in core 350, which is hypothesized to increase the effective impedance of coil 304. In an exemplary embodiment of the invention, the conductivity of core 350 is relatively reduced. Optionally, core 350 is processed, the processing potentially reducing the conductivity. In a not necessarily limiting example, core 350 is laminated (e.g., formed into thin layers separated by an insulating material, the layers arranged parallel to the direction of the expected magnetic flux lines). Inventors hypothesize that lamination of core 350 also reduces the eddy currents induced in core 350. In some cases, different materials are used for cap 318 to reduce eddy current formation.

In exemplary embodiment of the invention, to achieve the desired operation frequency, the capacitance and resistance in the circuit are selected according to the coil effective inductance and the ferromagnetic core. Note that the inductance is hypothesized to be affected by the ferromagnetic core and by the operation frequency. The general relation between the actual operation frequency $f_{act}$ and the inductance L, resistance R and capacitance C is given by:

$$f_{act} = \frac{1}{2\pi\sqrt{\frac{1}{LC} - \frac{R^2}{4L^2}}}$$

Exemplary Magnetic Field Parameters

In an exemplary embodiment of the invention, the coil producing the magnetic field is wound around the central axis of the enhancement device. To help understand the magnetic field produced by the enhancement device, the following cylindrical coordinates system is used:

Axial axis—An axis parallel to the implant top-down axis. Field component along this axis is termed "z component".

Radial axis—The radius vector from a point on the implant axis outward. Field component along this axis is termed "r component."

Phi axis—An axis tangential to the radius vector at any point. Field component along this axis is termed "phi component".

In an exemplary embodiment, the enhancement device is inserted inside a dental implant previously positioned inside the upper or lower jaw bones. To help understand locations relative to the jaw bone, the following terms are used:

"cervical"—along a line between the upper and lower jaws, and more particularly, along a line between the implant root and a covering of the implant device;

"coronal"—along a cervical line, toward the implant device covering;

"apical"—along a cervical line, toward the implant root; and

"radial"—along a line generally coinciding with the radius of the substantially circular implant device, or along a line parallel to a line generally coinciding with the radius of the substantially circular implant device, and substantially perpendicular to a cervical line.

In an exemplary embodiment of the invention, the coil having circular windings around the central axis of the device axis induces magnetic field mainly along the axial axis (z component), and a radial component around the coil top and bottom edges. The induced electric field will have mainly a phi component.

The terms described above are not necessarily limiting, but are used to help understand the described embodiment. Other embodiments may require other reference terms.

FIG. 7A is a graph of one example of an enhancing magnetic field, illustrating the discovery by the inventors of magnetic field parameters that cause acceleration in the bone regeneration process (e.g., osteogenesis) around the implant (e.g., dental implant), for example, as described in the section "EXAMPLES". FIG. 7B is an illustration of an exemplary bone enhancement device 200 creating the field illustrated in FIG. 7A. FIG. 7C is the raw data in table format used to draw the graph of FIG. 7A.

In an exemplary embodiment of the invention, the device is constructed so that it generates a magnetic field with the combination of the following properties:

Magnetic flux density is, for example, about 0.05-0.5 milliTesla (mT) at up to about 2 mm from the surface of the device, or for example, about 0.2-0.45 mT, or for example about 0.2-0.3 mT, or other smaller, intermediate or lager values at up to about 2 mm. For example, magnetic flux density of, for example, about 0.05-0.5 mT at up to about 1 mm from the surface of the device, or for example about 0.2-0.45, or for example about 0.2-0.3 mT, or other smaller, intermediate or larger values at up to about 1 mm.

In an exemplary embodiment of the invention, the magnetic flux density is located around at least, for example, about 90% of the length of the implant, or at least about 80% of the length, or at least about 70% of the length, or at least about 60% of the length, or at least about 50% of the length, or other smaller, intermediate or larger percentages. Alternatively or additionally, the magnetic field density is located at a jaw-bone depth (e.g., from the surface) of, for example, up to at least about 3 mm, or 4 mm, or 5 mm, or 7 mm, or 10 mm, or 13 mm, or other smaller, intermediate or larger depths. In an exemplary embodiment of the invention, the enhancement device is constructed and/or built to have the magnetic field flux density as mentioned above.

In an exemplary embodiment of the invention, the implant is cylindrical in cross section. In other embodiments, other shapes are used, for example, a square cross section.

In an exemplary embodiment of the invention, the magnetic fields lines primarily parallel to the long axis of the cylindrical implant. For example, not considering the direction of the magnetic field around the poles.

In an exemplary embodiment of the invention, the length of the implant producing the enhancing magnetic field is in contact with trabecular bone. Optionally or alternatively or additionally, the length is in contact with cortical bone.

In an exemplary embodiment the current pulse to produce the magnetic field has the following combination of parameters (optionally together with the magnetic field parameters):

Frequency of, for example, 0.5 Hz to 50 Hz, for example, from 10 Hz to 40 Hz.

Pulse duration of, for example about 12 microseconds to about 70 microseconds, or about 30 to 70 microseconds, or about 45 to 55 microseconds, or other smaller, intermediate or larger pulse durations. Optionally, the pulse is biphasic, for example comprised of a positive signal followed by a negative signal.

Repetition rate of the pulse, for example, continuously operating, single pulse, multiple pulses (e.g., preset number), or other repetition rates.

A duty cycle ratio (e.g., pulse duration as a ratio to one period, or 1/frequency) of, for example, about 1:1500-1:2400, or about 1:2000-1:2400, or other smaller, intermediate or larger duty cycles.

Peak to peak current amplitude of, for example, about 50-150 mA or about 50 mA-130 mA, or about 50-80 mA, or other smaller, intermediate or larger peaks.

Average pulse current of, for example, about 30-80 mA, or about 40-50 mA, or other smaller, intermediate or larger values.

Average current of about 3-15 mA, or about 5-10 mA, or other smaller, intermediate or lager values.

Pulse waveform, for example, sinusoidal, square, sawtooth, triangular.

In some embodiments, the current is continuously applied for a period of, for example, about 30-70 days, or about 50-70 days, or other smaller, intermediate or larger time values. Alternatively, the current is turned on and off during set times, for example, turned on at night before sleep and/or turned off upon waking up.

In an exemplary embodiment of the invention, the electrical field at the bone site within about 2 mm of the enhancement device is, for example, about 0.5-6 mV/cm, or about 1 to 4 mV/cm, or other smaller, intermediate or lager values.

In one example, the following set of parameters are used: a biphasic, sinusoidal current pulse of 50 microseconds produces the magnetic file around the implant. The current is produced with a peak to peak amplitude of about 130 mA. The pulse is followed by a wait period which is about 2000 times as long as the current pulse (for a total time of 0.1 seconds). The pulse and corresponding wait time are continuously repeated (e.g., frequency of Hz) for at least 50 days.

Energy Saving Mechanism

In an exemplary embodiment of the invention, one or more energy saving mechanisms are used. Optionally, an energy saving circuit is used. Optionally or additionally, the device is only activated when needed. Potentially, the energy saving mechanisms allow for the device to operate for the entire treatment duration, for example, at least 30 days, or at least 50 days, or at least 70 days, or other smaller, intermediate or larger time periods without replacing the power source. Potentially, the energy saving mechanisms allow for the use of small batteries that can fit inside the enhancement device and that will allow the device to operate for the treatment duration.

Energy Saving Circuit

Figure 8A:
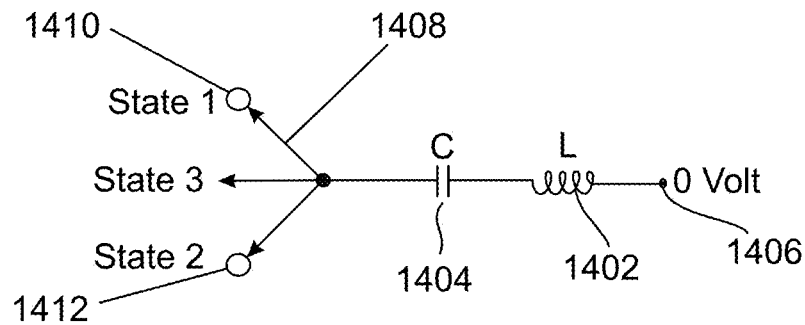
FIG. 8A is a schematic of an energy saving circuit, in accordance with an exemplary embodiment of the invention.
Figure 8B:
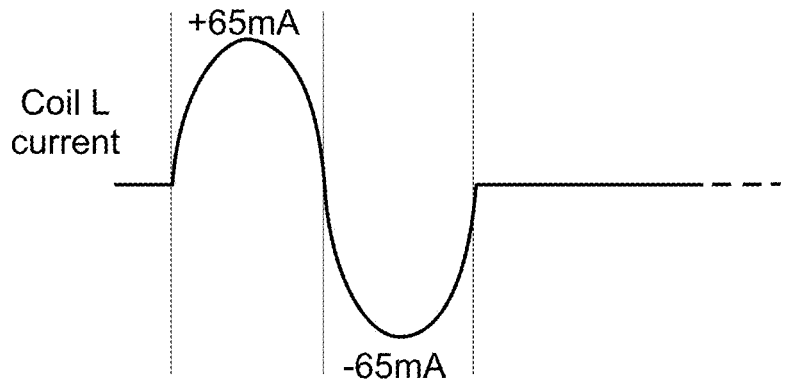
FIGS. 8B-C are graphs to help understand the function of the circuit of FIG. 8A.
Figure 8C:
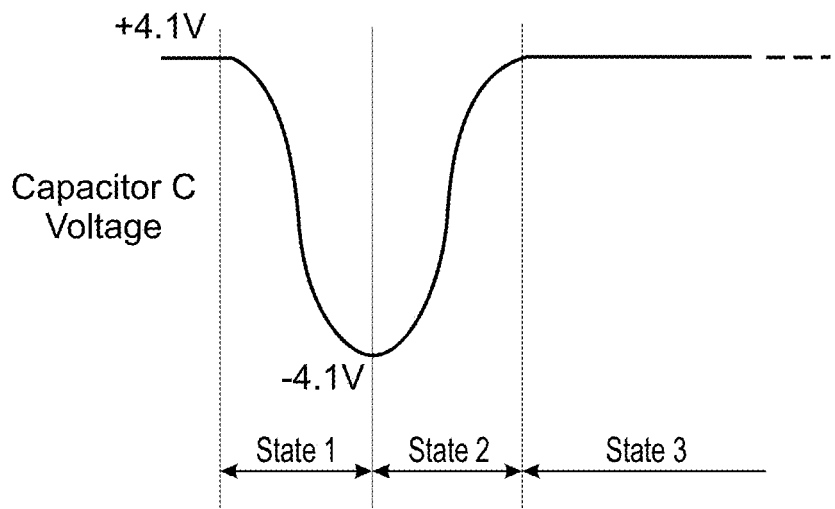

FIG. 8A is a simplified circuit diagram of the energy saving circuit comprising a coil 1402 (e.g., to generate the bone enhancing magnetic field) and a capacitor 1404 (e.g., to form a resonance circuit). FIG. 8B shows the current through coil 1402 during different circuit states of FIG. 8A. FIG. 8C shows the voltage of capacitor 1404 during different circuit states of FIG. 8A.

In an exemplary embodiment of the invention, the energy saving circuit drives a current through coil 1402 (to create the enhancing magnetic field), effectively forming a voltage drop across coil 1402, the value of the voltage drop being about double the voltage provided by the voltage source. In a not necessarily limiting example, the voltage provided by the power source (e.g., one or more batteries) is, for example, about 3.0 Volt, for example, each battery produces about 1.5 Volt.

Without being bound to theory, the energy saving circuit can be thought of as a pendulum able to maintain a high amplitude by providing a small amount of energy (e.g., push) on each swing as opposed to requiring multiple swings to get to the high amplitude during a time period required for the cycle. For example, before the start of the pulse, the pendulum is in the position having an amplitude above a reference. The amplitude represents potential energy of the pendulum, similar to the potential energy stored in the capacitor in the form of charges (e.g., Volts). To generate the pulse, the pendulum is released to swing. The energy of the moving pendulum represents the energy released by the capacitor in the form of the current through the coil. The returning pendulum will reach an amplitude slightly lower than the original release amplitude (e.g., due to energy losses such as friction and/or kinetic energy harnessed from the swing). To raise the pendulum back to the original amplitude, only a small amount of additional energy is required, for example, as compared to moving the pendulum from an amplitude of zero (e.g., no stored potential energy state). Correspondingly, only a small amount of charge needs to be added to the capacitor as opposed to a complete recharge. The pendulum is held storing the potential energy until the next release to generate the next pulse.

In an exemplary embodiment of the invention, the coil is not efficient in transmitting, so the energy not transmitted is collected and/or stored for use during the next transmission.

In an exemplary embodiment of the invention, the energy saving circuit saves energy when current is applied using very short and/or a small number of pulses followed by a long wait, for example, the ratio of the current pulses to the wait time is, for example, about 1:750 to about 1:5000, or about 1:2000 to about 1:2400, or other smaller, intermediate or larger values.

For comparison purposes, in an embodiment without the energy saving circuit, to reach the peak to peak current value of about 130 mA, one or more charging current pulses are applied (or using the pendulum concept, smaller swings). Due to the very short duty cycle, the charging currents are needed to reach the peak current values through the inductor. In one not necessarily limiting example, the peak of the charge current pulses (e.g., half sinusoid wave) in succession are: +22 mA, −29 mA, +36 mA, −42 mA, +50 mA, −57 mA until the peak values of +65 mA and −65 mA are reached. Without being bound to theory, the energy saving circuit eliminates the need for the charging pulses.

Referring back to FIGS. 8A-C, the capacitor is maintained charged to the highest voltage capable by the batteries (e.g., shown in a not necessarily limiting manner as +4.1 V, for the 3.0 Volt total capacity). The charged state of the capacitor can be through of as the pendulum held at the highest amplitude. The positive charged state is referred to as state 3.

To create the current pulse through coil 1402, a switch 1408 connects capacitor 1404 to a negative voltage source 1410 (e.g., reverse polarity of the battery, or about −3 V), also referred to as state 1. As shown in FIG. 7C, the voltage across capacitor 1404 swings from the positive to the negative highest voltage values (e.g., from +4.1 Volt to −4.1 Volt). Correspondingly, the current through coil 1402 rises from 0 to the highest current value (e.g., +65 mA according to the circuit parameters). The state change can be through of as the pendulum swinging from one amplitude to the other side.

Switch 1408 causes a change from state 1 to state 2, connecting capacitor 1404 to the positive voltage source 1412. Capacitor 1404 swings back from the lowest negative voltage to the highest positive voltage (e.g., from −4.1 Volt to +4.1 Volt). Correspondingly, the current through coil 1402 falls from 0 to the lowest current value (e.g., −65 mA). The effective current through coil 1402 is the sum of the absolute value of the highest and lowest values (e.g., 65+65=130 mA). The current provides the bone enhancing electromagnetic field. The state change can be through of as the pendulum swinging back from the other side to the original position. Switch 1408 causes a change from state 2 back to state 3, removing capacitor 1404 from any voltage source, and trapping the highest voltage value in capacitor 1404 (e.g., +4.1 Volt). Capacitor 1404 is held in state 3 until the next scheduled pulse. The state can be through of as the pendulum held in the original position with the original amplitude, ready for another release.

In some embodiments, the enhancement device is programmed to improve energy efficiency. Optionally, the device is programmed to only function during the night, for example, in patients that sleep with their mouths closed, the mouth does not cool and energy is preserved. Alternatively, the device is programmed to function only during the day, for example, in patients that sleep with their mouths open, the energy consumption would increase due to the cooling effect of the air in the mouth.

Exemplary Magnetic Switch

Figure 9:
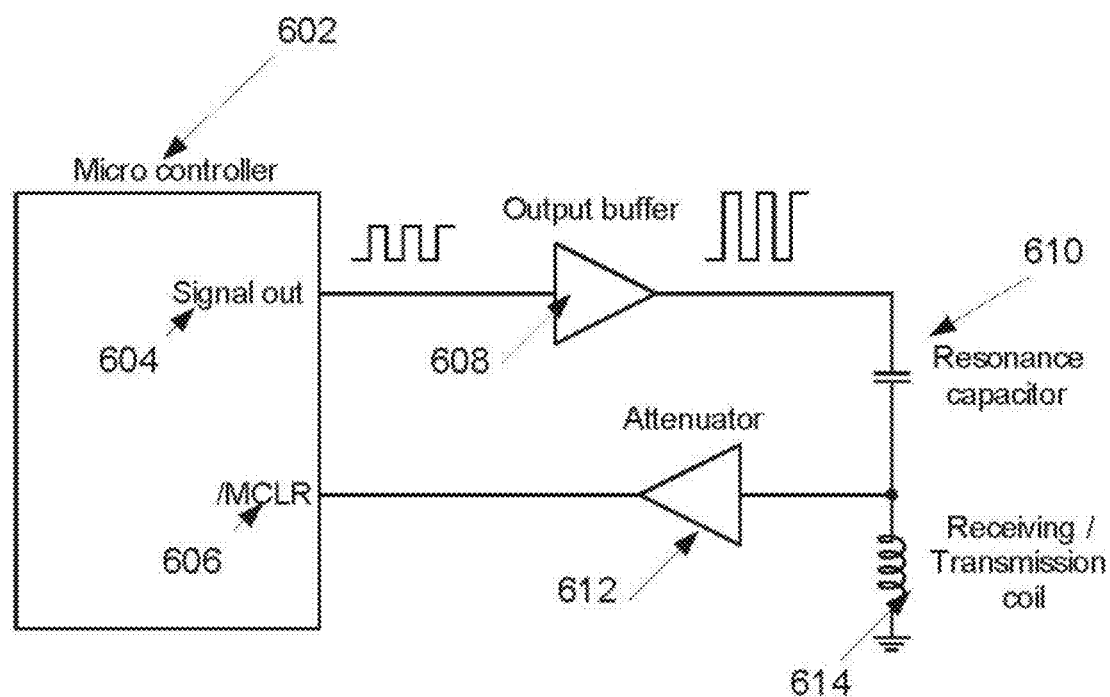
FIG. 9 is a circuit diagram of circuitry to control the enhancement device, in accordance with an exemplary embodiment of the invention.

FIG. 9 is a simplified diagram of a circuit having a magnetic switch, in accordance with an exemplary embodiment of the invention. Optionally, the magnetic switch activates a controller 602. Optionally, controller 602 controls a magnetic field transmitter (e.g., a coil 614) to emit the enhancement magnetic field. A potential advantage of the magnetic switch is selective remote activation to preserve battery life, for example, to provide a relatively long shelf life and/or only activate the device when needed.

In some embodiments, the magnetic switch can be used with other implant types, for example, devices adapted for insertion into bone and/or bone implants, for example, orthopedic devices, for example, to enhance bone fixation, and/or fracture healing. Potentially, the same advantages apply, for example, of preserving battery life.

In an exemplary embodiment of the invention, controller 602 is programmed. Optionally, controller 602 arrives unprogrammed (e.g., from the manufacturer) and is programmed before insertion. Alternatively, the programming is done to adjust one or more stored parameters (e.g., stored on a memory coupled to the controller). Some not necessarily limiting examples of programming options include; pulse frequency, pulse duration, amplitude of magnetic field, how often to leave on magnetic field (e.g., turn on only at night and turn off during the day). Optionally, controller 602 can be turned off (e.g., to sleep state).

In an exemplary embodiment of the invention, the programming is done by the externally applied magnetic field. Optionally, the magnetic field is coded (e.g., by variations in wait time between pulses), and the controller decodes the message to program itself.

In an exemplary embodiment of the invention, the magnetic switch is activated by an externally applied magnetic field. Optionally, the remote signals are received on the same coil that is used to generate the bone enhancing electromagnetic field.

In an exemplary embodiment of the invention, the circuit comprises an attenuator 612 to prevent self activation of controller 602, for example, during normal operation of the device to produce the magnetic field.

In an exemplary embodiment of the invention controller 602 produces output signal 604, for example, as described herein. Optionally, an output buffer 608 filters the output signal. In an exemplary embodiment, a resonance capacitor 610 is used to control the frequency of magnetic field produced by coil 614.

In an exemplary embodiment of the invention, controller 602 is placed in a sleep mode. For example, consuming no more than about 10 nA, or 20 nA, or 30 nA, or 50 nA, or 100 nA, or other smaller, intermediate or larger currents. The low currents are possible using the energy saving circuit, for example, as described with reference to FIG. 11. In an exemplary embodiment of the invention, batteries provide controller 602 with enough power so that controller 602 is able to remain in the sleep mode for at least 1 year, at least 3 years, at least 5 years, or other smaller, intermediate or larger time frames. In some embodiments, during sleep mode, the controller is activated by a pulse on its reset input ("Master Clear"—MCLR input). Optionally, the magnetic switch controls the passing of the pulse on the reset input. Optionally, the switch is activated by an external magnetic field. In some embodiments, during an active operation mode, attenuator 612 prevents the MCLR input, for example to prevent self reset of the enhancement device.

In some embodiments, controller 602 is programmed to measure time intervals between pulses. Optionally, the time intervals are decoded to a data protocol for controlling activation and/or deactivation of the device.

In a not necessarily limiting scenario, the enhancement device is assembled by the manufacturer. Optionally, the device is manufactured and shipped in a hermetically sealed packaged, for example, to ensure sterility and quality of the device. The batteries have been installed and in electrical communication with the circuitry of the device. Before implantation in the patient, the device is activated (e.g., as described herein), for example, by the treating physician and/or dentist. Optionally the device is activated when still in wrapping, potentially preserving the sterility of the device until insertion. Optionally, the device is activated by placing the device in a hole in the cradle.

In an exemplary embodiment of the invention, controller 602 is remotely activated by a signal received on coil 614 that is also used to produce the selected magnetic field. Optionally, coil 614 produces a voltage due to an externally applied magnetic field. Optionally, the externally applied field is applied from a distance and/or without contacting coil 614, for example, by the cradle as described herein. Alternatively, in some embodiments, a separate coil not used to produce the magnetic field is used to receive the signal. Potentially, use of the single coil to transmit and receive saves spaces and allows the circuitry to reside inside the small volume.

In an exemplary embodiment of the invention, a sufficiently strong externally applied magnetic field produces a voltage by coil 614, the voltage being high enough to trigger activation of controller 602 at a trigger signal input 606. Alternatively, in some embodiments, the external magnetic field produces a smaller signal that is then amplified and optionally undergoes a comparison by a comparator before entering input 606. Potentially, use of the strong external field does not require the additional components, reducing power requirements and space.

In an exemplary embodiment of the invention, an attenuator 612 in electrical communication between coil 614 and input 606 is selected to only allow voltages above a voltage threshold to be transmitted to input 606. Optionally, the voltage threshold is selected so that voltages higher than the threshold trigger input 606 (e.g., will trigger a state change). In an exemplary embodiment, the voltage threshold is selected to be above the voltage at input 606 that is created during regular operation of the device (e.g., generation of therapeutic magnetic field by coil 614). Optionally attenuator 612 is, for example, one or more resistors, transistors, inductors and/or combinations thereof. The resistance of the resistor is selected according to the selected voltage threshold and according to other circuit elements, for example the value of resonance capacitor 610. Potentially, attenuator 612 prevents triggering controller 602 during device operation (e.g., treatment). Potentially, attenuator 612 also prevents waste during regular use. By reducing the input signals, the processor requires less energy to operate to process the input signals.

In an exemplary embodiment of the invention, a first signal at input 606 triggers controller 602 to change from the sleep mode to the active mode, the active mode allowing data processing and/or delivering the stimulating magnetic field. Optionally, a second signal at input 606 triggers controller 602 to change from the active mode back to the sleep mode. Alternatively or additionally, a sequence of signals at input 606 programs controller 602, for example, with magnetic field parameters and/or current parameters.

In an exemplary embodiment of the invention, the signal applied by the external magnetic field is encoded and is decoded by controller 602 (after entering input 606). Optionally, software and/or circuitry keeps controller 602 in the active state after each pulse received at input 606 to allow decoding. In a not necessarily limiting example, the code comprises of a set value or sequence of time intervals between pulses. Potentially, the coded signal prevents inadvertent activation and/or deactivation of controller 602, for example, by non-intentional externally applied magnetic fields.

In some embodiments, controller 602 and/or another external device charges the battery inside the enhancement device. Optionally, controller 602 charges the batteries by wireless charging (e.g., inductive charging), for example, by using the transmitting and/or receiving coil.

In an exemplary embodiment of the invention, the enhancement system comprises a transmitter for remote activation of the electromagnetic switch. Optionally, the transmitter is in the shape of a cradle, for example, the enhancement device is inserted into a hole and a button is pressed to activate the magnetic switch. Alternatively, the transmitter is shaped for placement inside the mouth against the tooth, for example, placed inside a soft material so that it can be bitten and secured in position against the tooth or when the mouth is open. Alternatively, the transmitter is placed near the implant from outside of the mouth, for example, against the skin of the cheek.

FIG. 10A is a top view, FIG. 10B is an isometric view, and FIG. 10C is a cross sectional side view of a remote activator (e.g., cradle 300) for activation of the enhancement device, in accordance with an exemplary embodiment of the invention. Cradle 300 is designed to interact with the circuit of FIG. 9, for example, FIG. 10C shows an enhancement device 622 being activated by cradle 300.

In an exemplary embodiment of the invention, cradle 300 comprises a hole 302 sized and shaped to accommodate at least some of a portion of enhancement device 622 comprising coil 614. Alternatively, device 622 is activated while still in package 624 (e.g., clear plastic cylindrical box), for example, to preserve sterility of device 622 during the activation. Optionally, some space is allowed between walls of hole 302 and coil 614 and/or walls of package 624.

In an exemplary embodiment of the invention, hole 302 is surrounded by a transmitter (e.g., coil 620), and/or the transmitter is to the side of hole 302. Current flowing through transmitter coil 620 induces a magnetic field inside hole 302. The induced magnetic field induces a voltage sufficiently high voltage across coil 614 to activate controller 602, for example, as described with reference to FIG. 9.

In an exemplary embodiment of the invention, coil 620 around hole 302 is used to detect the state of the enhancement device, for example, if the device is functioning or not. Optionally, if coil 614 is producing the therapeutic magnetic field, a current through coil 620 around hole 302 is detected. Alternatively, if coil 614 is not producing the therapeutic magnetic field, there is no current through hole coil 620. Alternatively, the correct function of therapeutic device 622 in producing the therapeutic magnetic field is detected according to the magnitude and/or pattern of the induced current through hole coil 620.

In some embodiments, the cradle is used to test the power level generated by the implant. Optionally, the power level is just measured. Alternatively, the device is optionally first turned on by the cradle, the power level is measured by the cradle, and then the device is optionally turned off by the cradle.

In an exemplary embodiment of the invention, input 306 (e.g., button, microphone for voice activation) allows for the user to control the activation of the enhancement device. Optionally, pressuring button 306 powers coil around hole 302 and changes the state of the enhancement device, for example, from sleep to active. Optionally or additionally, a second press re-activates coil around hole 302 and changes the state of the enhancement device again, for example from active back to sleep.

Alternatively, no input is provided, with activation/deactivation occurring automatically by cradle 300 upon insertion of the enhancement device into hole 302.

In an exemplary embodiment of the invention, output 304 (e.g., LED, speaker for audio output) allows the user to determine the state of the enhancement device. Optionally, the sleep state of the enhancement device is indicated. Optionally or additionally, the active state of the enhancement device is indicated. Optionally or additionally, the power status of cradle 300 is shown, for example, if cradle 300 is plugged in and/or batteries are providing sufficient power for operation.

In some embodiments, cradle 300 comprises a communication link (e.g., wireless and/or wired, e.g., USB) to a computer terminal (e.g., laptop, remote server, internet web site). Optionally, programming of the enhancement device is provided through software on the computer terminal, with uploading and downloading to the enhancement device provided through cradle 300. Optionally or additionally, cradle reads an ID code from the device for billing purposes. Optionally or additionally, the cradle reports activity via the internet, USB connection, or other communication channels. Optionally or additionally, the cradle is connected to a computer to provide a programming interface.

Exemplary Circuit

Figure 11:
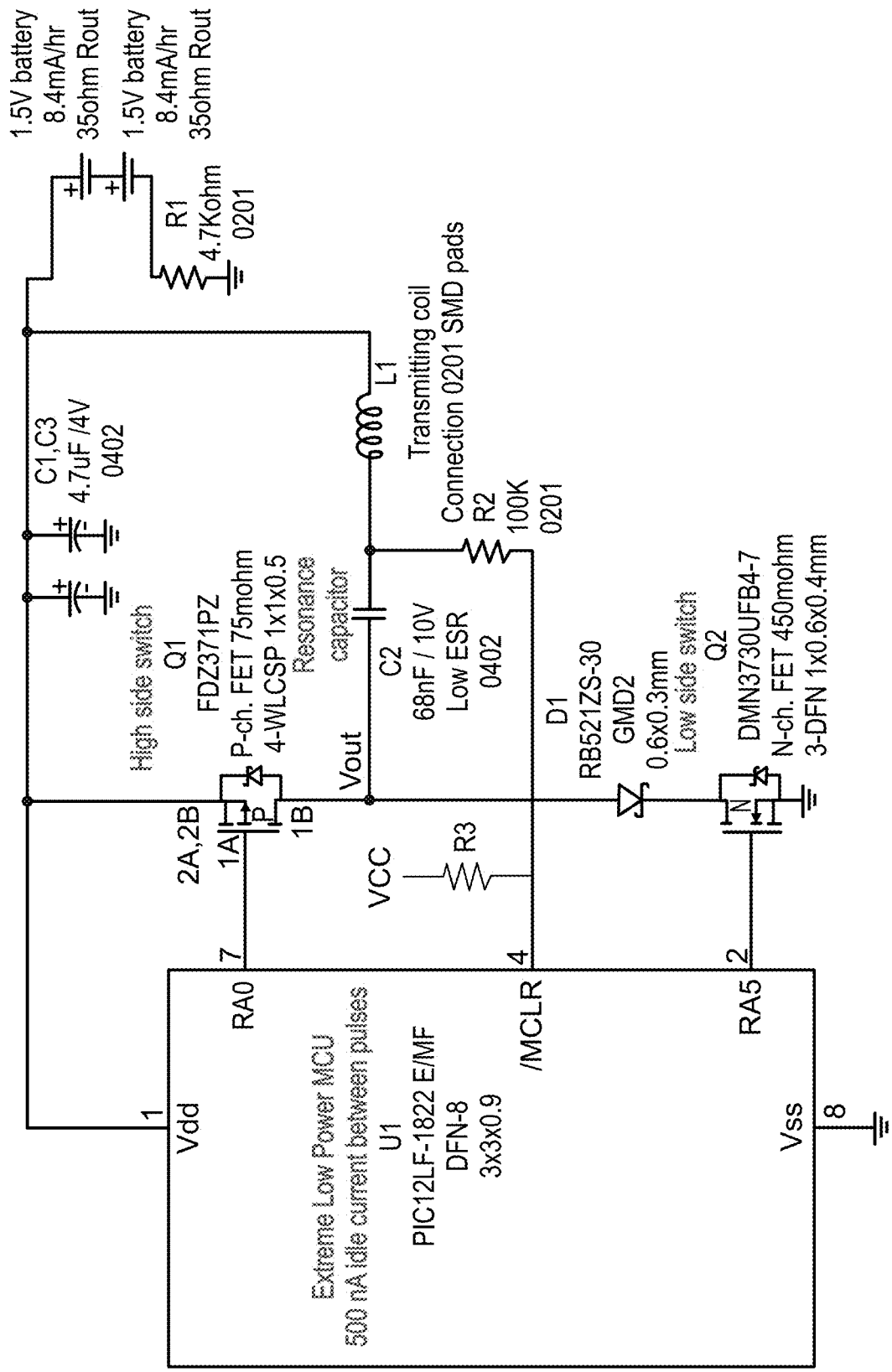
FIG. 11 is a circuit diagram of an energy saving mechanism, in accordance with an exemplary embodiment of the invention.

FIG. 11 is an exemplary circuit diagram, illustrating the control of the formation of the magnetic field with the optional energy saving designs.

In an exemplary embodiment of the invention, U1 is a controller to control application of current to the coil to form the enhancement magnetic field, for example, as described herein. U1 is connected to ground through Vss and to batteries through Vdd. Optionally, U1 is a very low power consumption controller, for example, consuming no more than about 30 nA in sleep mode and/or 500 nA in active mode between pulses. In some not necessarily limiting examples, U1 is implemented as an application specific integrated circuit (ASIC), or general circuitry programmed by software.

In an exemplary embodiment of the invention, L1 is a coil that provides the therapeutic electromagnetic field when current is provided through the coil.

In an exemplary embodiment of the invention, L1 is in series with capacitor C2.

In an exemplary embodiment of the invention, voltage at Vout is connected to either RA0 (positive voltage) or by RA5 (negative voltage). Optionally, switches Q1 and Q2 control the state changes of C2, for example, as described in the section "Energy saving circuit". Optionally, state 3 is achieved by Q1 and Q2 being off. Optionally or additionally, state 1 is achieved by activation of Q1. Optionally or additionally, state 2 is achieved by deactivation of Q1 and activation of Q2. In one example Q1 and/or Q2 are implemented as transistors, for example, field effect transistors (FET).

In an exemplary embodiment of the invention, R2 is in parallel with C2. Optionally, R2 acts as the attenuator described in the section "Magnetic Switch". In an exemplary embodiment of the invention, R2 and C2 serve as a resonance circuit to generate the required frequency through L1. Optionally, the values of R2 and/or C2 are selected according to the selected frequency through L1.

In some embodiments, R3 is in parallel with R2. Optionally, R3 further acts as the attenuator (e.g., together with R2) described in the section "Magnetic Switch".

In some embodiments, D1 is a Zener diode in series between Q1 and Q2. Optionally, D1 defines the current direction.

In some embodiments, R1 is in series with the batteries and ground. Optionally, R1 compensates for the internal resistance of the batteries.

In some embodiments, C1, C3 are capacitors in parallel with the batteries and the rest of the circuit. Optionally, C1 and C3 help to prevent rebound currents.

Various embodiments and aspects of the present invention as delineated hereinabove and as claimed in the claims section below find experimental and/or calculated support in the following examples.

EXAMPLES

Reference is now made to the following examples, which together with the above descriptions illustrate some embodiments of the invention in a non limiting fashion.

Bone Enhancement Experiment

Purpose:

To test the ability of the exemplary enhancement device (e.g., shown in FIG. 7B) to stimulate bone healing and bone density around implants.

Materials:

The bone enhancement device of FIG. 7B comprising an induction coil designed to fit inside a 5*6 mm (diameter*length) healing cap compatible with regular platform internal-hex dental implants. The coil consists of a 40 um-thick wire making 133 turns in 4 layers around a 0.75*7.5 mm (diameter*length) ferrite core. Optionally, other parameters of the coil and/or core may be used. For example, in some embodiments, the thickness of the coil may range between 30-80 um, for example 35 um, 50 um, 75 um or intermediate thicknesses. Optionally, in some embodiments, the coil may be arranged in a different number of layers, for example 3 layers, 6 layers, 2 layers or intermediate number of layers. Optionally, in some embodiments, the number of turns of the coil around the ferrite core may range between 80-250, for example 90, 140, 189, or intermediate numbers. Optionally, in some embodiments, the dimensions of the ferrite core may include, for example, a diameter ranging between 0.5-1 mm, such as 0.6, 0.7, 0.9 mm, or intermediate values, and a length ranging, for example, between 5-10 mm, such as 6 mm, 5.5 mm, 9 mm or intermediate values.

The device was programmed using the exemplary parameters described in the example in the section "Exemplary Magnetic Field Parameters". Also used was a commercially available dental implant.

Animals:

Twenty four 4-month old male New Zealand White rabbits.

Methods:

6 rabbits were implanted with the device for 2 weeks, and 6 animals served as controls. Another 6 rabbits were implanted with the device for 4 weeks, and another 6 animals served as controls. The dental implants were inserted into the proximal metaphysic of one tibia in each of the animals. The site is easily accessible, composed mainly of trabecular bone, and is a well established model for dental implants. The enhancement device was threaded on the treatment group, and an empty device was threaded on the control group.

Figures 12A, 12B:
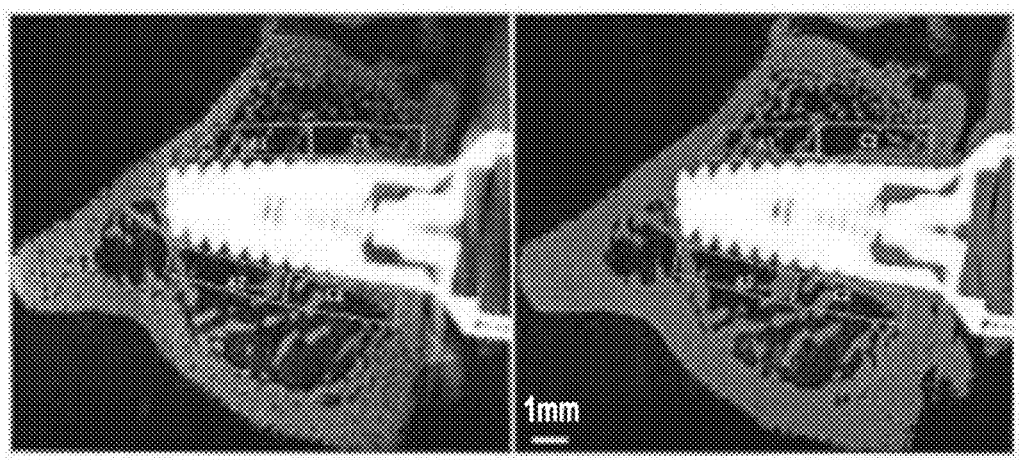
FIGS. 12A-12B are CT scans to help understand an experiment, in accordance with an exemplary embodiment of the invention.

At the time of sacrifice, the proximal 20 mm of the tibiae including the implant were scanned using a 3D x-ray microscopy system XCT400 (Xradia, Calif., USA). Peri-implant bone density was measured on 2D tomographs (close to the middle axis of the implant shank). Trabecular bone volume density was measured using NIH ImagJ software. The peri-implant region was divided into two subregions, where the region from the healing abutment to half the length of the implant was defined as the "coronary" region, and the distant half as the "apical" region (FIG. 12A, where A1-A2 are the apical regions and C1-C2 are the coronary regions). In the radial dimension, the region extended from 0.1 mm to 1.1 mm from implant surface. The cortical bone and the part of the implant shank in contact with cortical bone were excluded from the analysis. Bone was segmented out of the surrounding soft tissues and implant using a thresholding procedure (FIG. 12B is the segmentation of FIG. 12A). Bone response was separately calculated for the coronary and the apical peri-implant regions.

An additional 3D analysis was later performed. The three dimensional analysis enabled assessing the newly formed bone volume. Various parameters such as a percentage of bone to implant contact (BIC or osteointegration percentage OI), the number of trabeculae (Tb.N), the tribecular thickness (Tb.Th), and tribecular spacing (Tb.Sp) were measured in a range of 1 mm surrounding the implant.

Results:

Two Dimensional Analysis Results

The vector summation of the magnetic field along the implant axis at 1 and 2 mm from implant surface is detailed in FIG. 7C and changes in the magnetic field intensity are graphically presented in FIG. 7A. The measured magnetic field intensity was relatively higher in the coronary area than the apical area as described in FIGS. 12A-12B. The coronary region being at less than 1 mm away radially from the implant surface, and at a distance from the start of the screw (corresponding to bone depth) of between about 4 to 7 mm.

Figures 13A, 13B:
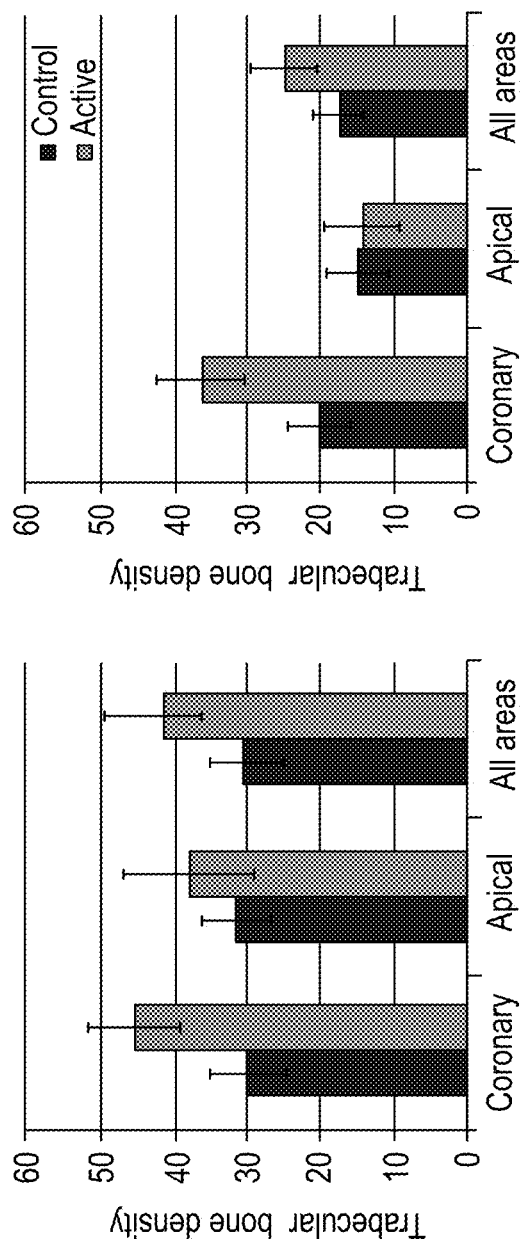
FIGS. 13A-13B are graphs of the experimental results based on a two dimensional analysis.

FIG. 13A graphically represents the results of the 2 week group, and FIG. 13B graphically represents the results of the 4 week group. FIG. 14 is a sample of some exemplary CT scans from the 2 week and 4 week active and control groups, showing higher trabecular bone density around implants in the active group.

The results show that at 2 weeks, there was a 51% increase in the trabecular bone volume density of the coronary region in the test group as compared to the control group (p=0.043, FIG. 13A). Bone density in the apical region increased by 20% in the test group relative to the controls.

At 4 weeks, there was no difference in density around the apical area between treatment and control groups. However, bone density around the coronary area of devices in the test group was further stimulated to values 78% higher than in the control group (p=0.019, FIG. 13B).

When calculating the entire peri-implant region (apical and coronary), the treatment group experienced an increased peri-implant trabecular bone density of 35% and 43% after 2 and 4 weeks, respectively, as compared to control (p=0.124 and 0.112, respectively).

In the control group between 2 and 4 weeks post-surgery (bone remodeling phase), peri-implant trabecular bone density decreased from 31.2% to 17.7% (i.e. bone density decreased by 43%, p=0.025), due to a decrease of 53% and 33% in the apical and coronary subregions, respectively (FIGS. 13A-13B). In the test group, bone remodeling was also observed at a very similar extent as bone density decreased by 40% (p=0.048).

Three Dimensional Analysis Results

Figure 15:
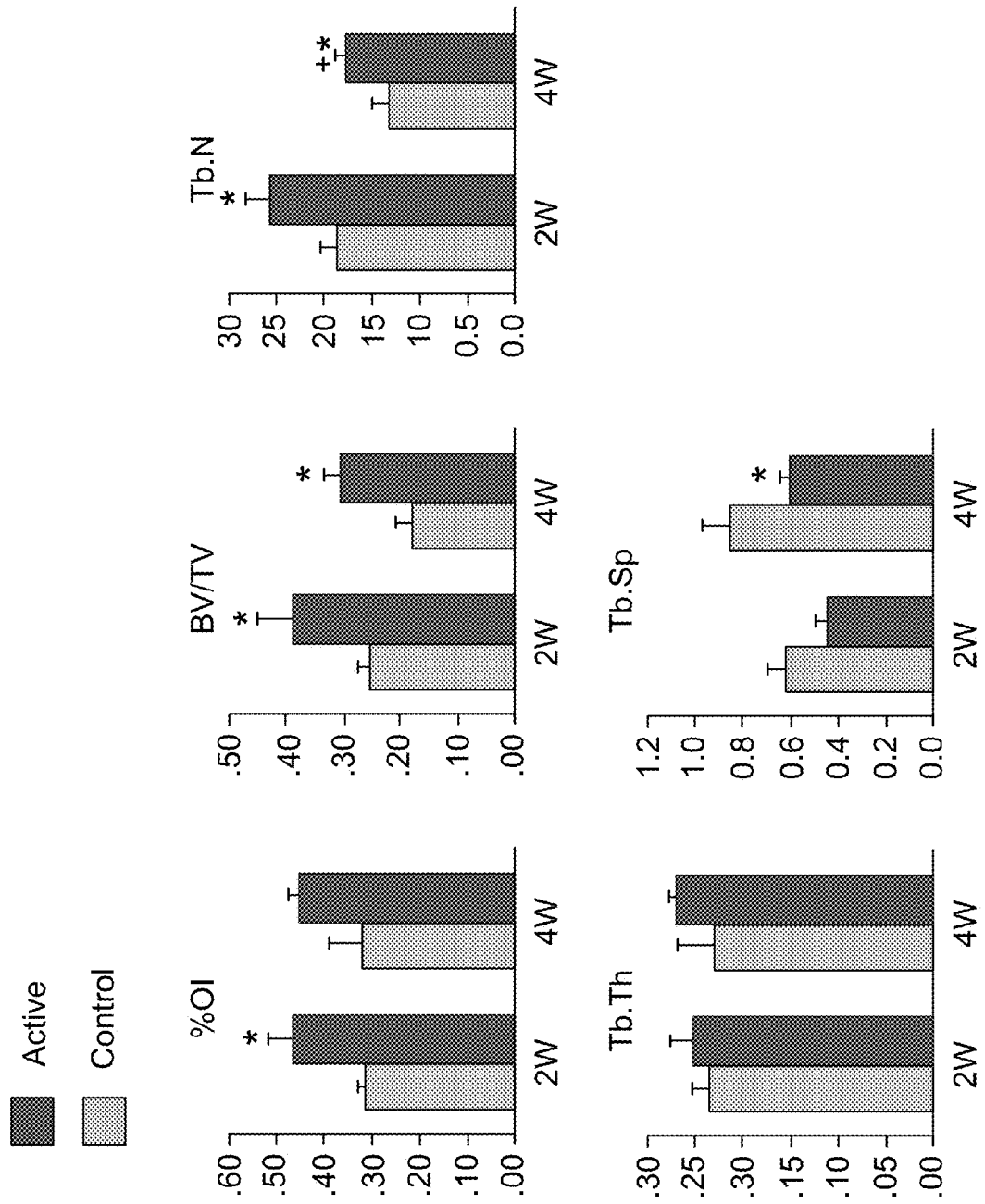
FIG. 15 is a graphical representation of results based on a three dimensional analysis.

FIG. 15 graphically represents the results of various parameters that were measured at 2 weeks and 4 weeks post implantation. At 2 weeks post implantation, there was a 56% increase in trabecular bone volume density (BV/TV) of the coronary region in the active group as compared to the control group. Additionally, there was a 44% increase in the number of trabeculae, and a 48% increase in the BIC (OI) in the active group as compared to the control group.

At 4 weeks post implantation, there was a 62% increase in trabecular bone volume density (BV/TV) of the coronary region in the active group as compared to the control group. The BIC(OI) remained steady with a 48% increase in the active group as compared to the control group. A 32% decrease was measured in trabecular spacing (Tb.Sp) in the active group as compared to the control group, indicating the rise in bone density. The trabecular thickness (Tb.Th) remained almost unaffected. The increase in bone volume density in the active group as compared to the control group indicates an approximately 3 times faster bone formation in the active group.

Figure 16A:
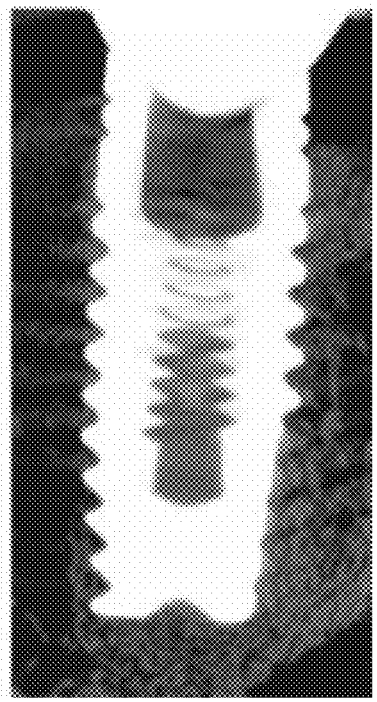
FIG. 16A-D show some exemplary CT scans to help understand the experimental results.
Figure 16B:
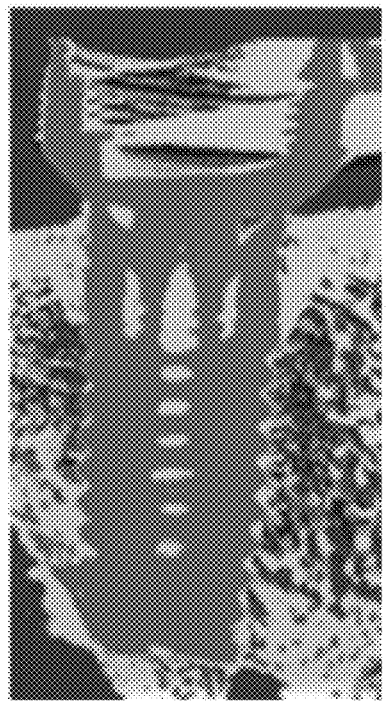
Figure 16C:
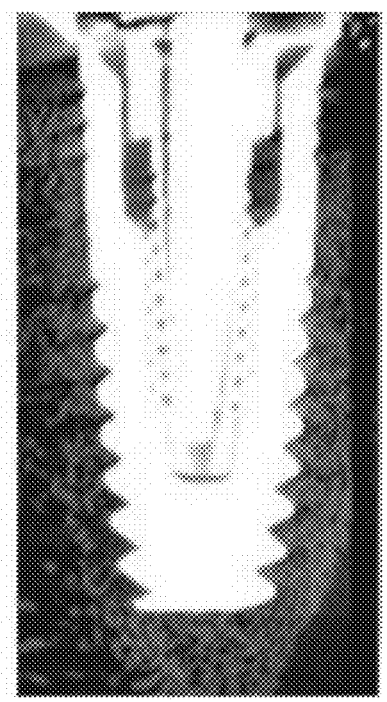
Figure 16D:

FIGS. 16A-D are some exemplary CT images of the active and control groups, showing higher trabecular bone density around implants in the active group. FIGS. 16A and 16B are images of the control group. FIGS. 16C-D are images of the active group. FIGS. 16A and 16C are 2D images (of a single slice), while FIGS. 16B and 16D are 3D images obtained by reconstructing and layering multiple slice images, for example 150 slice images. Higher bone density in the bone surrounding the implant can be observed, for example, on FIG. 16D as opposed to FIG. 16B.

No noticeable signs of infection, inflammation or decay were observed in any of the groups.

CONCLUSION

Results from both two dimensional and three dimensional analysis support the hypothesis that the selected magnetic field produced by the enhancement device increases bone density at least at a distance of about 2 mm from the surface of the implant and at a bone depth of about 4-7 mm. The depth of about 4-7 mm is significant, as this region is particularly sensitive to bone resorption due to concentration of mechanical stress during occlusal loading.

Furthermore, results support the hypothesis that the stimulation device did not impair bone remodeling.

As was shown in the 3D analysis, all tested parameters such as the number of trabeculae, the bone to implant contact, the trabecular spacing and other measured parameters indicate an increasing and accelerated peri-implant osteogenesis in the active group as compared to the control group.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

General

It is expected that during the life of a patent maturing from this application many relevant bone enhancement devices will be developed and the scope of the term enhancement device is intended to include all such new technologies a priori.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A system for bone enhancement comprising:
   a device adapted for insertion into a bone implant, said device including
   a housing including an implantable portion sized and shaped for implantation into the bone,
   a first transmitter at least partially inserted into said implantable portion of said housing, said first transmitter arranged to transmit at least a bone enhancing magnetic field for said bone enhancement and
   a magnetic switch coupled to activate said first transmitter to an active state that continues for a treatment period, said magnetic switch activated by an external magnetic field and said first transmitter remaining in said active state after removal from said external magnetic field; and
   a cradle having a recess sized and shaped to fit said device, said cradle including
   second transmitter arranged to produce said external magnetic field.

2. The system of claim 1, wherein said first transmitter is configured for magnetic pulses at a repetition rate of 0.5 Hz to 50 Hz.

3. A system as in claim 1, wherein said first transmitter comprises at least one wire coil wound and stacked around a core and at least partially inserted into said implantable portion of said housing, said wire coil configured to produce said bone enhancing magnetic field.

4. The system of claim 3, wherein said first transmitter is configured for applying a current having a peak amplitude from 50 mA to 150 mA to said wire coil to produce said bone enhancing magnetic field.

5. A system as in claim 3, further comprising:
   a controller disposed in said device controlling said first transmitter, and
   a receiver connected to said wire coil for receiving an external magnetic field coded for programming said controller.

6. The system of claim 3, wherein a number of windings of said wire coil, a diameter of a wire of said wire coil and a number of wires stacked around said core are selected to reduce heating while transmitting said bone enhancing magnetic field.

7. A system as in claim 6, wherein said device is sized and arranged for insertion in a jaw bone implant for an artificial tooth, said device extending to an end of a cavity of said implant.

8. A system as in claim 6, wherein a diameter of said at least one wire ranges from about 10 μm to about 80 μm, a diameter of a winding of said wire coil around said core is about 800 μm to about 1150 μm, and a number of windings of said wire around said core ranges from about 450 to about 550.

9. A system as in claim 6, wherein said heating of said bone and said bone enhancing magnetic field are selected to synergistically increase osteointegration in said bone, wherein said bone is heated by about 0.02 degrees Celsius to about 3 degrees Celsius during steady state.

10. A system according to claim 6, wherein said device comprises an energy saving circuit, said circuit comprising:
    a capacitor in series with said wire coil, said capacitor being able to store sufficient charge to pass a current through said coil to produce said bone enhancing magnetic field;
    one or more switches in series with said capacitor; and
    a controller to:
      control said switches to maintain said capacitor at a first voltage value during a non-pulse phase, wherein no significant magnetic field is produced,
      control said switches to charge said capacitor to a second voltage value, said second voltage value equal to about said first voltage value, said second voltage value having a charge opposite to said first voltage value; and
      control said switches to charge said capacitor from said second voltage value back to said first voltage value, said charging occurring over a time period of a pulse phase, wherein said charging said capacitor comprises passing a current through said coil to produce said bone enhancing magnetic field, said current related to a voltage drop across said coil of about two times said first voltage.

11. A system as in claim 10, wherein a voltage source of about 3 Volt is used, wherein at least one of said first voltage value and said second voltage value is charged within about 25 microseconds, and wherein a peak current is reached during a single voltage swing.

12. The system of claim 1, further comprising:
    an attenuator arranged to prevent self reset of said first transmitter.

13. A system as in claim 1, wherein said external magnetic field is arranged for wirelessly charging batteries in said device.

14. The system of claim 1, wherein said first transmitter is configured for applying said bone enhancing magnetic field having a magnetic flux density of about 0.05-0.5 mT at up to at least about 2 mm from a surface of said implant.

15. A system for bone enhancement comprising
    a device adapted for insertion into a bone implant, said device comprising:
    a housing including an implantable portion sized and shaped for implantation into the bone
    a first transmitter at least partially inserted into said implantable portion of said housing, said first transmitter arranged to transmit at least a bone enhancing magnetic field for said bone enhancement;
    a magnetic switch coupled to activate said first transmitter to an active state that continues for a treatment period, said magnetic switch activated by an external magnetic field and said first transmitter remaining in said active state after removal from said external magnetic field and
    a second transmitter arranged to produce said external magnetic field; said second transmitter including a cradle shaped and sized to stand stably on a flat structure and for mechanically engaging said device to support said device while activating the device with said external magnetic field outside of said bone implant.

16. The system of claim 15, wherein said first transmitter is configured to produce around said implant said bone enhancing magnetic field having a magnetic flux density of about 0.05-0.5 mT at up to at least about 2 mm from a surface of said implant.

17. A system as in claim 15, wherein said cradle is shaped and sized to support said device while the device is inside a sterile package.

18. A system as in claim 15, wherein said cradle comprises at least one of an input for allowing remote activation of said device by a user, and an output for allowing a user to determine a state of said device.

19. The system as in claim 15, wherein said device is sized and arranged for insertion in a jaw bone implant for an artificial tooth, said device extending to an end of a cavity of said implant.

20. The system of claim 15, wherein said first transmitter is configured for magnetic pulses at a repetition rate of 0.5 Hz to 50 Hz.

21. A system for bone enhancement comprising:
a device adapted for insertion into a bone implant, said device including
a housing including an implantable portion sized and shaped for implantation into the bone,
a first transmitter at least partially inserted into said implantable portion of said housing, said first transmitter arranged to transmit at least a bone enhancing magnetic field for said bone enhancement and
a magnetic switch coupled to activate said first transmitter to an active state that continues for a treatment period, said magnetic switch activated by an external magnetic field and said first transmitter remaining in said active state after removal from said external magnetic field;
a second transmitter arranged to produce said external magnetic field; and
a testing circuit including a coil for testing the power level generated by said implantable device by measuring a current induced by the bone enhancing magnetic field on the coil.

22. The system of claim 21, wherein said first transmitter is configured to produce around said bone implant said bone enhancing magnetic field having a magnetic flux density is at least one of: about 0.2-0.45 mT at up to at least about 1 mm from a surface of said implant, and about 0.2-0.3 mT up to at least about 2 mm from said surface.

23. The system of claim 21, wherein said said first transmitter is configured to produce said bone enhancing magnetic field having a pulse duration that ranges from about 30 to 70 microseconds followed by a wait time that is 1500-2400 times as long as said pulse duration.

24. The system of claim 21, wherein said said first transmitter is configured to produce a a biphasic, sinusoidal pulse of current to produce said magnetic field.

25. The system of claim 21, wherein said first transmitter is configured for magnetic pulses at a repetition rate of 0.5 Hz to 50 Hz.

26. A system as in claim 21, further comprising:
an attenuator arranged to prevent self reset of said first transmitter.

* * * * *